(12) United States Patent
Justis et al.

(10) Patent No.: US 8,221,426 B2
(45) Date of Patent: Jul. 17, 2012

(54) METHODS AND DEVICES FOR DEFORMITY CORRECTION

(75) Inventors: Jeff R. Justis, Germantown, TN (US); John Stewart Young, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1192 days.

(21) Appl. No.: 12/029,670

(22) Filed: Feb. 12, 2008

(65) Prior Publication Data
US 2009/0204159 A1 Aug. 13, 2009

(51) Int. Cl.
*A61B 17/70* (2006.01)
(52) U.S. Cl. .................................... 606/86 A
(58) Field of Classification Search .................. 606/914, 606/916, 86 A, 87, 99, 246–279, 86 R, 90, 606/86 B; 600/210
See application file for complete search history.

(56) References Cited

U.S. PATENT DOCUMENTS

| | | | | |
|---|---|---|---|---|
| 5,445,641 | A * | 8/1995 | Frigg et al. .................. | 606/86 R |
| 5,735,851 | A | 4/1998 | Errico et al. | |
| 7,160,300 | B2 | 1/2007 | Jackson | |
| 2001/0053914 | A1 * | 12/2001 | Landry et al. ................... | 606/99 |
| 2004/0039384 | A1 | 2/2004 | Boehm, Jr. et al. | |
| 2004/0122437 | A1 * | 6/2004 | Dwyer et al. ................... | 606/87 |
| 2004/0215190 | A1 | 10/2004 | ANguyen et al. | |
| 2005/0033299 | A1 * | 2/2005 | Shluzas ........................... | 606/61 |
| 2005/0065517 | A1 | 3/2005 | Chin | |
| 2005/0154389 | A1 | 7/2005 | Selover et al. | |
| 2005/0171540 | A1 * | 8/2005 | Lim et al. ........................ | 606/61 |
| 2005/0277934 | A1 | 12/2005 | Vardiman | |
| 2006/0009775 | A1 * | 1/2006 | Dec et al. ........................ | 606/86 |
| 2006/0217735 | A1 * | 9/2006 | MacDonald et al. ........... | 606/90 |
| 2006/0235389 | A1 * | 10/2006 | Albert et al. .................... | 606/61 |
| 2006/0247630 | A1 | 11/2006 | Iott et al. | |
| 2006/0271050 | A1 | 11/2006 | Piza Vallespir | |
| 2007/0016188 | A1 | 1/2007 | Boehm, Jr. et al. | |
| 2007/0016198 | A1 | 1/2007 | Boehm, Jr. et al. | |
| 2007/0016199 | A1 | 1/2007 | Boehm, Jr. et al. | |
| 2007/0016200 | A1 | 1/2007 | Jackson | |
| 2007/0043359 | A1 | 2/2007 | Altarac et al. | |
| 2007/0073294 | A1 | 3/2007 | Chin et al. | |
| 2007/0093846 | A1 * | 4/2007 | Frigg et al. ..................... | 606/90 |
| 2007/0213715 | A1 * | 9/2007 | Bridwell et al. ................ | 606/61 |
| 2007/0213716 | A1 * | 9/2007 | Lenke et al. .................... | 606/61 |
| 2008/0097436 | A1 * | 4/2008 | Culbert et al. .................. | 606/61 |

FOREIGN PATENT DOCUMENTS

| | | |
|---|---|---|
| FR | 2857850 A1 | 1/2005 |
| WO | WO2006104813 A2 | 10/2006 |
| WO | WO2007092797 A2 | 8/2007 |

OTHER PUBLICATIONS

International Search Report and Written Opinion for PCT/US2009/033538 mailed on May 6, 2009.

* cited by examiner

*Primary Examiner* — Eduardo C Robert
*Assistant Examiner* — Atiya Mahmud

(57) ABSTRACT

An adapter including a coupling portion defining a lumen to receive a pedicle post, an intermediate portion including a first end fixedly attached to a side of the coupling portion and including a second end distal from the coupling portion, and a bolt. A proximal end of the bolt is rotatably coupled to the second end of the intermediate portion and a distal end of the bolt includes a connector.

26 Claims, 27 Drawing Sheets

METHODS AND DEVICES FOR DEFORMITY CORRECTION

FIELD OF THE DISCLOSURE

The present disclosure relates generally to orthopedics and orthopedic surgery. More specifically, the present disclosure relates to methods and devices for spinal deformity correction.

BACKGROUND

In human anatomy, the spine is a generally flexible column that may take tensile and compressive loads. The spine also allows bending motion and provides a place of attachment for tendons, muscles and ligaments. Generally, the spine is divided into four sections: the cervical spine, the thoracic or dorsal spine, the lumbar spine, and the pelvic spine. The pelvic spine generally includes the sacrum and the coccyx. The sections of the spine are made up of individual bones called vertebrae. Also, the vertebrae are separated by intervertebral discs, which are situated between adjacent vertebrae.

Misalignment of the spine may cause serious, sometimes crippling, problems, reducing quality of life for a patient. In particular, genetic defects and spinal injury may lead to scoliosis of the spine. Such a condition may lead to further injury such as disc or facet joint degeneration. As a result, if the deformity is not initially crippling, it may become so over time. To correct such deformity, surgery is typically used.

However, such surgeries tend to utilize large incisions and extensive tissue retraction. In many typical surgeries, muscle and ligament tissues are retracted or are surgically detached during the surgery and reattached afterward. As a result, such surgeries lead to long recovery time, patient discomfort, an increased risk of infection, and high expense.

As such, an improved apparatus and method for performing spinal surgeries would be desirable.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In a particular embodiment, a system for correcting spinal deformity includes a pedicle system, an adapter, and a multipoint alignment system. In an example, the pedicle system includes a pedicle screw or other pedicle coupling device coupled to a pedicle post extending from a surface of the pedicle. An adapter includes a receiving portion defining an opening to receive the pedicle post. In an example, the receiving portion includes a quick release mechanism to couple with the pedicle post. In addition, the adapter may include a pivotable coupling, such as a threaded coupling for engaging a holder and nut. The holder may be configured to hold a component of a multipoint alignment system.

In a further example, a method includes coupling a pedicle post to a pedicle, coupling the adapter to the pedicle post, coupling the holder to the adapter, and aligning the vertebrae. More than one pedicle post may be coupled to vertebrae of the patient. Each of the pedicle posts may be interconnected using the adapter and holder to apply pressure on the spine and align the vertebrae.

Description of Relevant Anatomy

Figure 1:
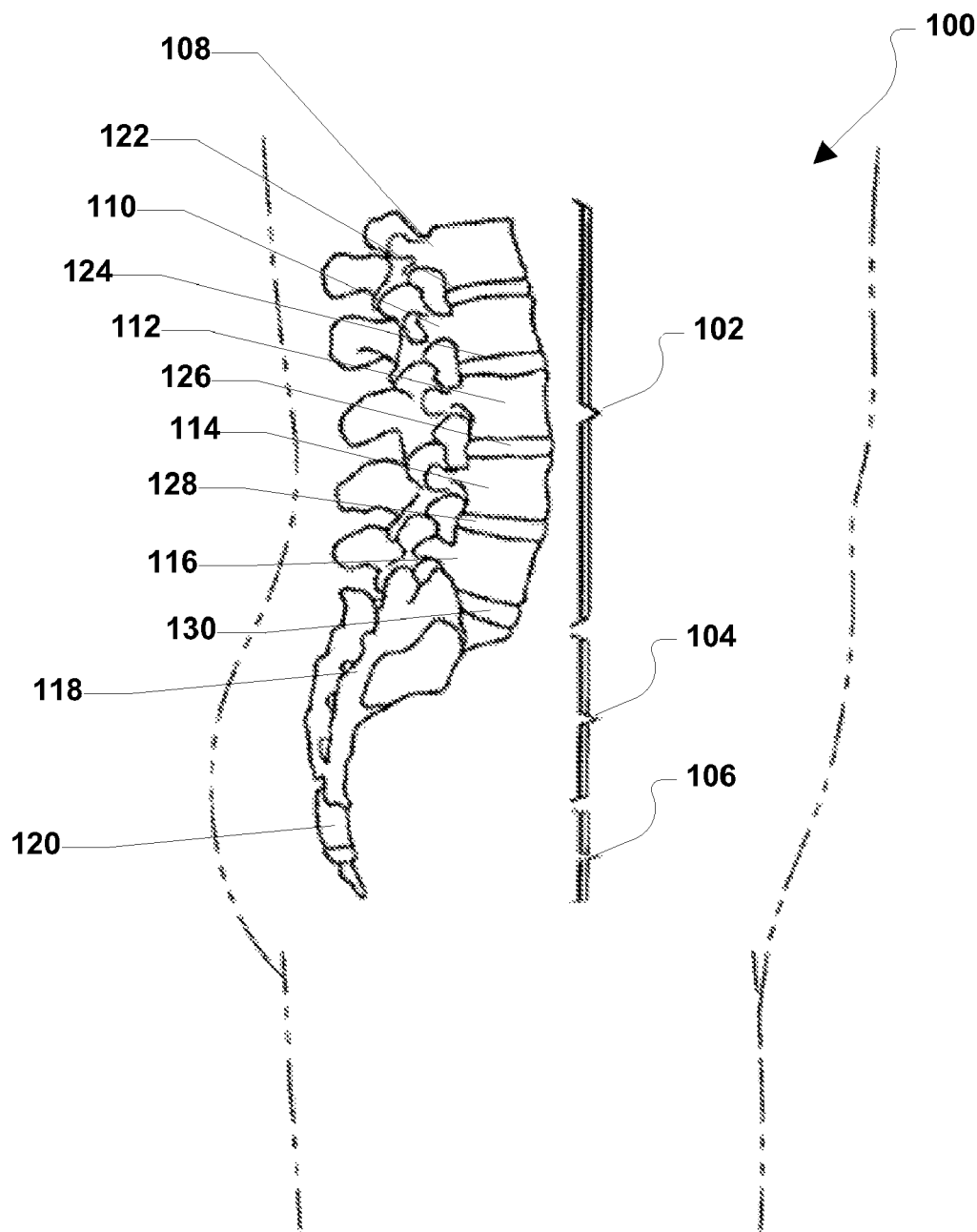
FIG. 1 includes an illustration of a lateral view of a portion of a vertebral column.

Referring initially to FIG. 1, a portion of a vertebral column, designated 100, is illustrated. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if the vertebrae (e.g., vertebrae 108, 110, 112, 114, and 116) are out of alignment or scoliotic, the spine may be treated in accordance with one or more of the embodiments described herein.

Figure 2:
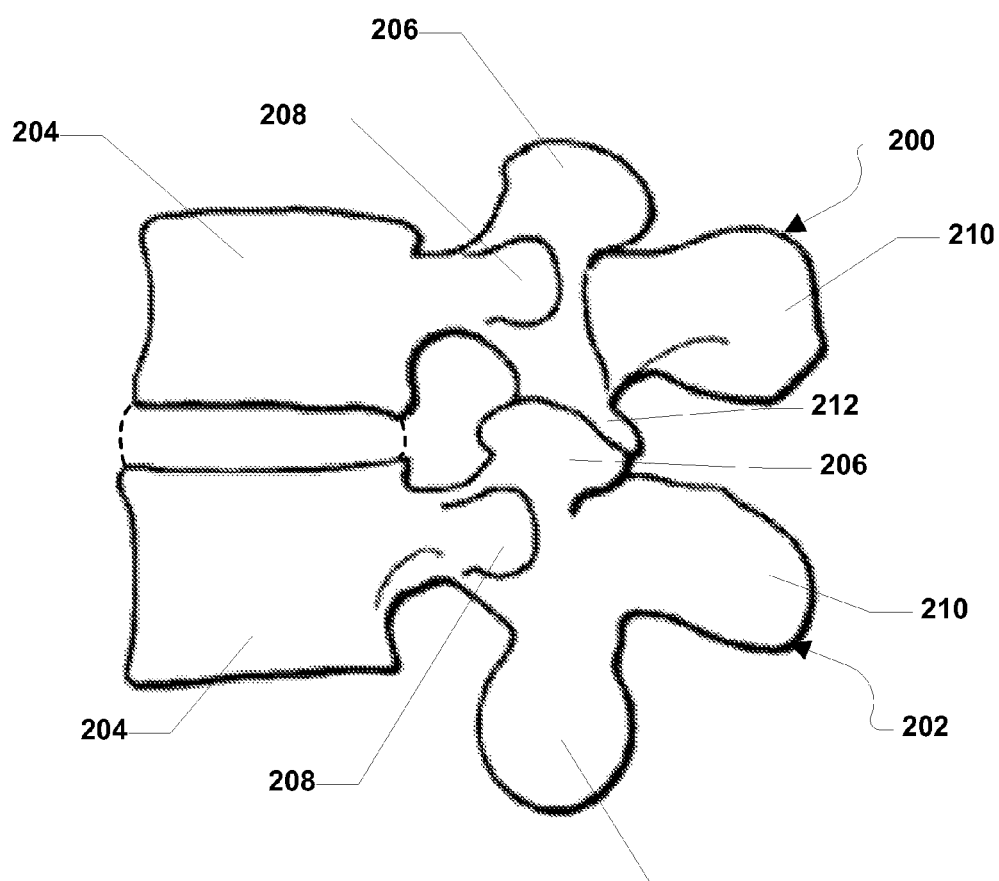
FIG. 2 includes an illustration of a lateral view of a pair of adjacent vertebrae.

FIG. 2 depicts a detailed lateral view of two adjacent vertebrae, e.g., two of the lumbar vertebra 108, 110, 112, 114, 116 illustrated in FIG. 1. FIG. 2 illustrates a superior vertebra 200 and an inferior vertebra 202. As illustrated, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202.

Figure 3:
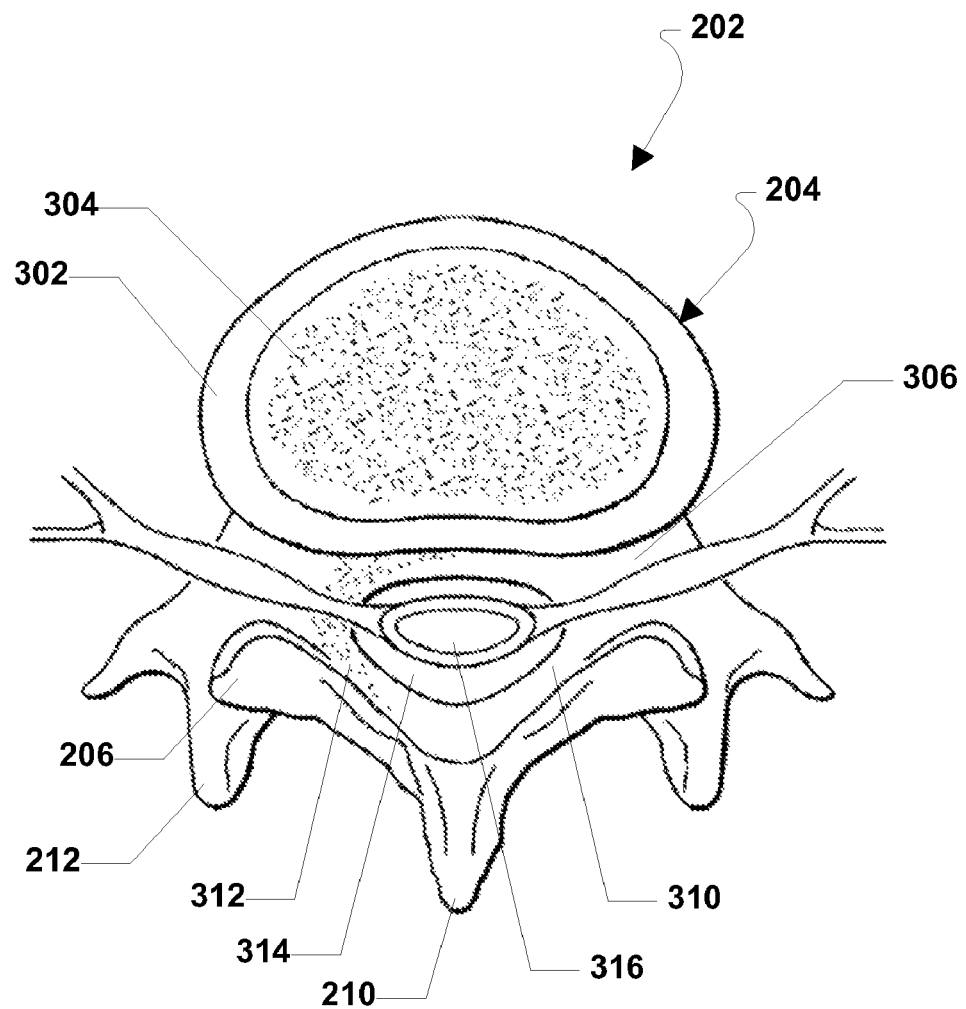
FIG. 3 includes an illustration of a top plan view of a vertebra.

Referring to FIG. 3, a vertebra, e.g., the inferior vertebra 202 (FIG. 2), is illustrated. As illustrated, the vertebral body 204 of the inferior vertebra 202 includes a cortical rim 302 composed of cortical bone. In addition, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

The vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Figure 4:
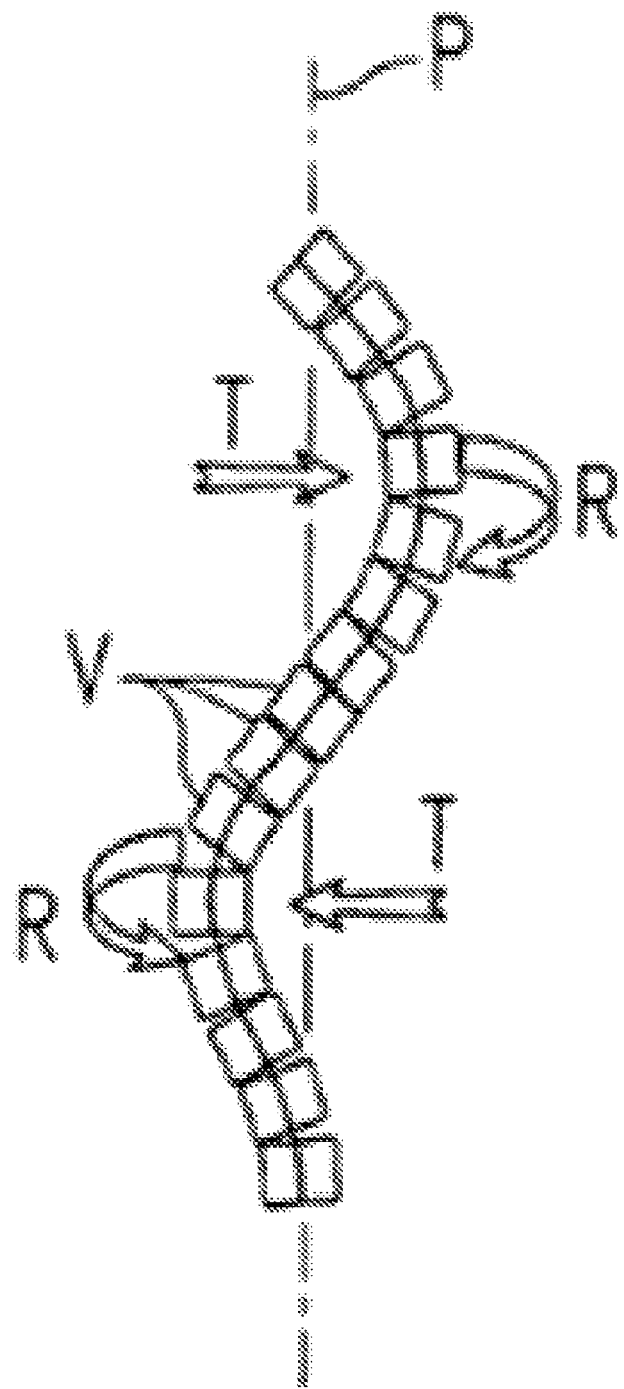
FIG. 4 includes an illustration of a scoliotic spine wherein the natural position and alignment of the vertebrae are altered due to abnormal vertebral translation and rotation.
Figure 5:
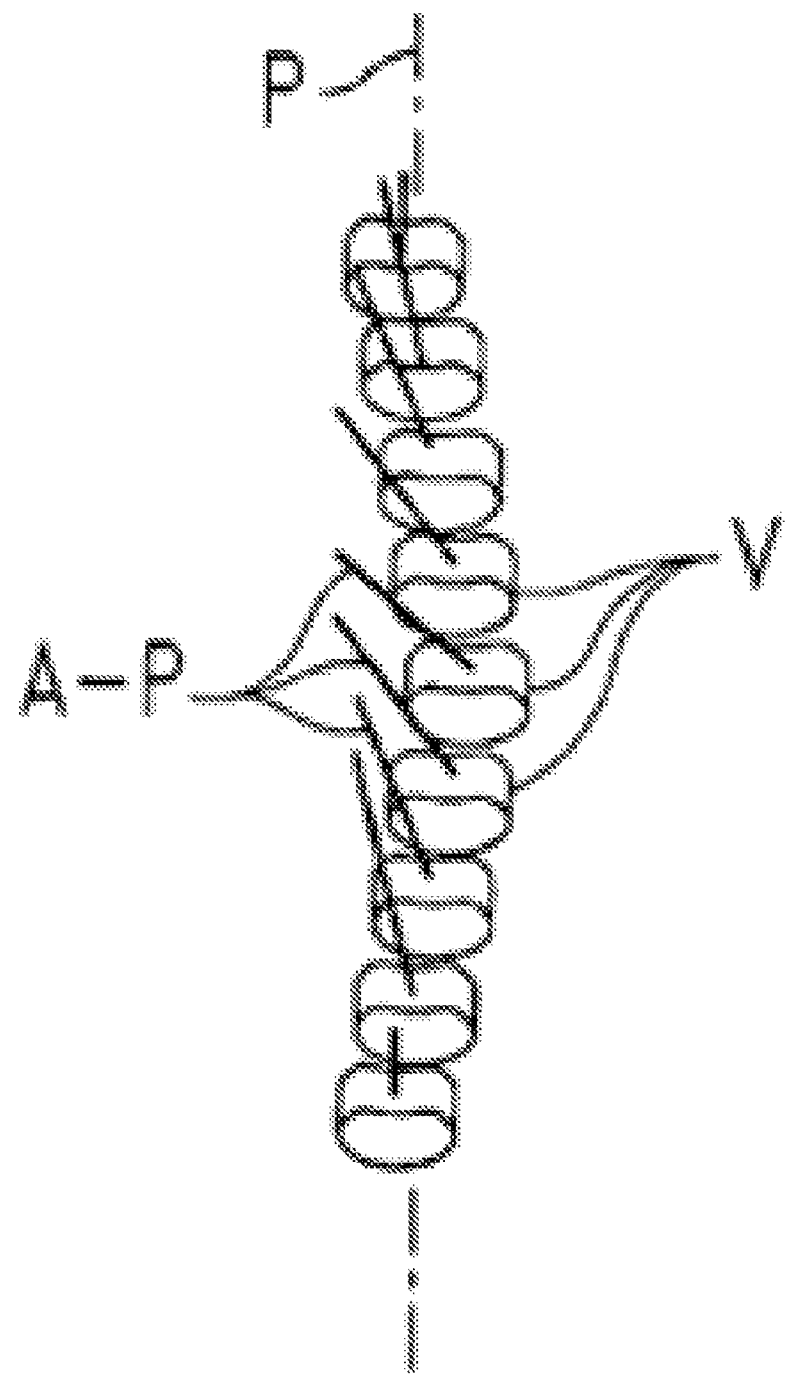
FIG. 5 includes an illustration of a scoliotic spine wherein the anteroposterior axes of the vertebrae are illustrated in a non-coplanar arrangement.

Referring to FIGS. 4 and 5, illustrated therein is a scoliotic spine including a number of vertebrae V. In a scoliotic spine, the natural position and alignment of the vertebrae V are altered due to abnormal vertebral rotation (depicted by arrows R) and abnormal vertebral translation (depicted by arrows T). As a result, the anteroposterior axes A-P of the vertebrae V, which are normally positioned within a common plane P (i.e., the sagittal plane), are non-coplanar (i.e., extend along multiple planes). Additionally, in a scoliotic spine, the thoracic spine is typically lordotic, thereby resulting in abnormal divergence of the anteroposterior axes A-P of the thoracic vertebrae.

Description of an Adapter

Figure 6:
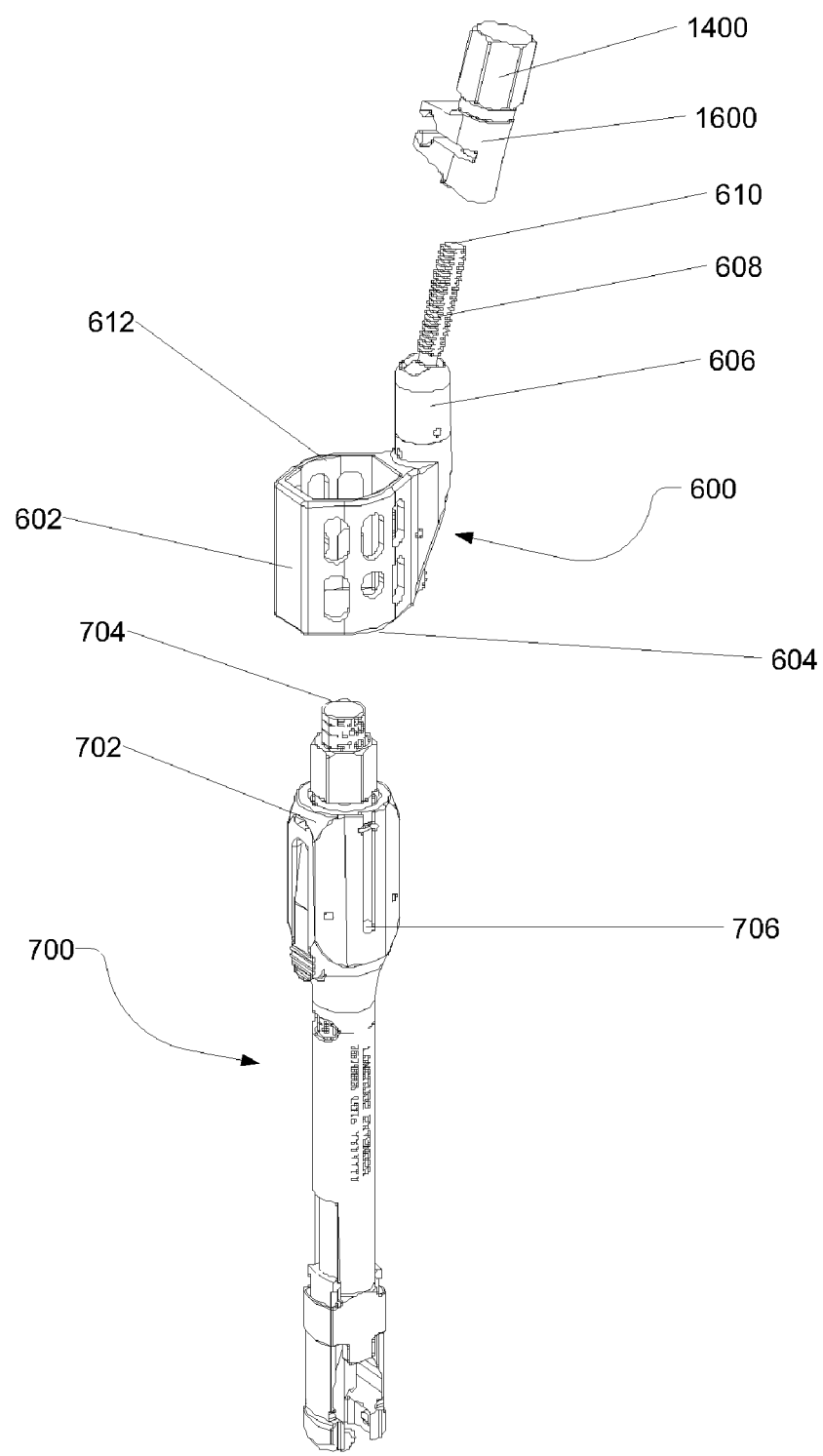
FIG. 6 includes an illustration of a perspective view of a pedicle post and an adapter.
Figure 7:
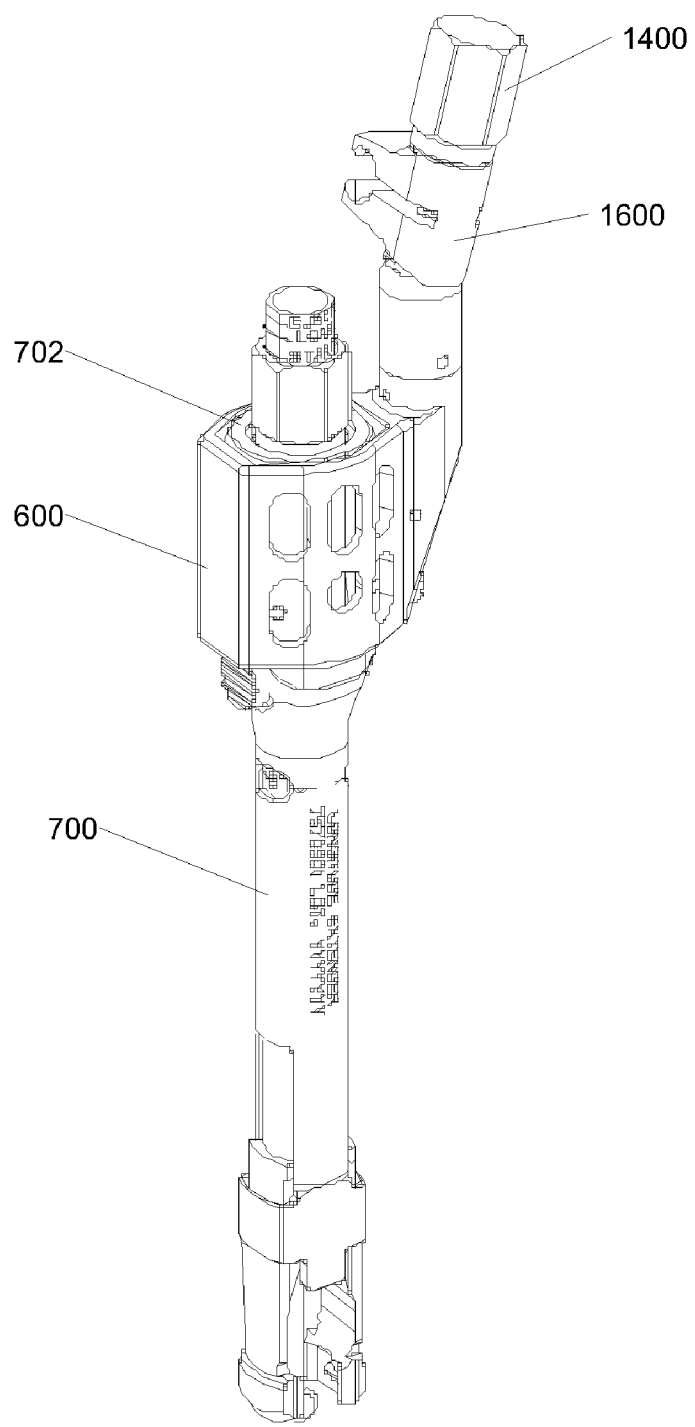
FIG. 7 includes an illustration of a perspective view of a pedicle post coupled to an adapter.
Figure 8:
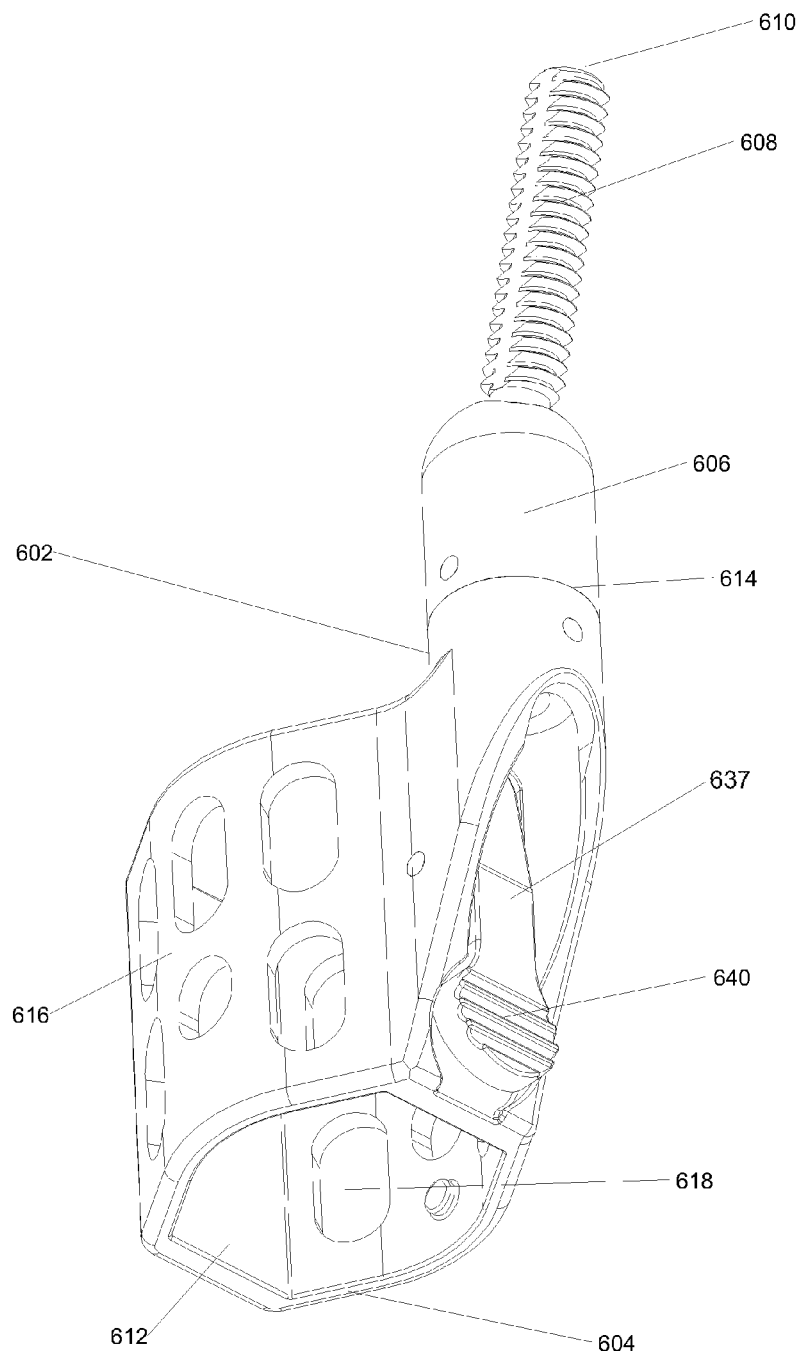
FIG. 8 includes an illustration of a perspective view of an adapter.

Referring to FIGS. 6 and 7, an adapter 600 is configured to couple to a pedicle post 700. The adapter 600 may include a coupling portion 602 at a proximal end 604, an intermediate portion 606, and a connector, such as a bolt 608 at the distal end 610. A holder 1600, configured to engage a rod, and a second connector, such as a nut 1400, may secure the holder 1600 to the connector, such as the bolt 608, as illustrated in FIG. 7.

The coupling portion 602 may include a lumen 612 to engage the pedicle post 700. The pedicle post 700 may include a head 702 at the distal end 704. The head 702 may have a non-circular shape and may include an indentation 706. The lumen 612 may have a non-circular shape complementary to the head 702 of the pedicle post 700. As illustrated in FIG. 7, the coupling portion 602 may engage the pedicle post 700.

Referring to FIG. 8, FIG. 9, FIG. 10 and FIG. 11, the adapter 600 is illustrated in more detail. In an example, the coupling portion 602 may have an attachment portion 614 to couple with the intermediate portion 606 and may have a cage portion 616 defining the lumen 612. In addition, the cage 616 may include a plurality of side openings 618. The lumen 612 is configured to receive the pedicle post 700, as illustrated in FIG. 7. In particular, when a pedicle post 700 engages the coupling portion 602 of the adapter 600, relative movement of the adapter 600 and pedicle post 700 is limited in both the axial and rotational directions.

The intermediate portion 606 may be rotatably coupled to the bolt 608. For example, the intermediate portion 606 may be coupled to the bolt 608 using a ball and socket joint 620. In an example, the bolt 608 may rotate about an axis. Alternatively, the bolt 608 may rotate about more than one axis. While alternative embodiments are envisages, the bolt 608 is generally depicted as having a threaded connector in this particular embodiment. Alternatively, other types of connectors may be used.

Figure 9:
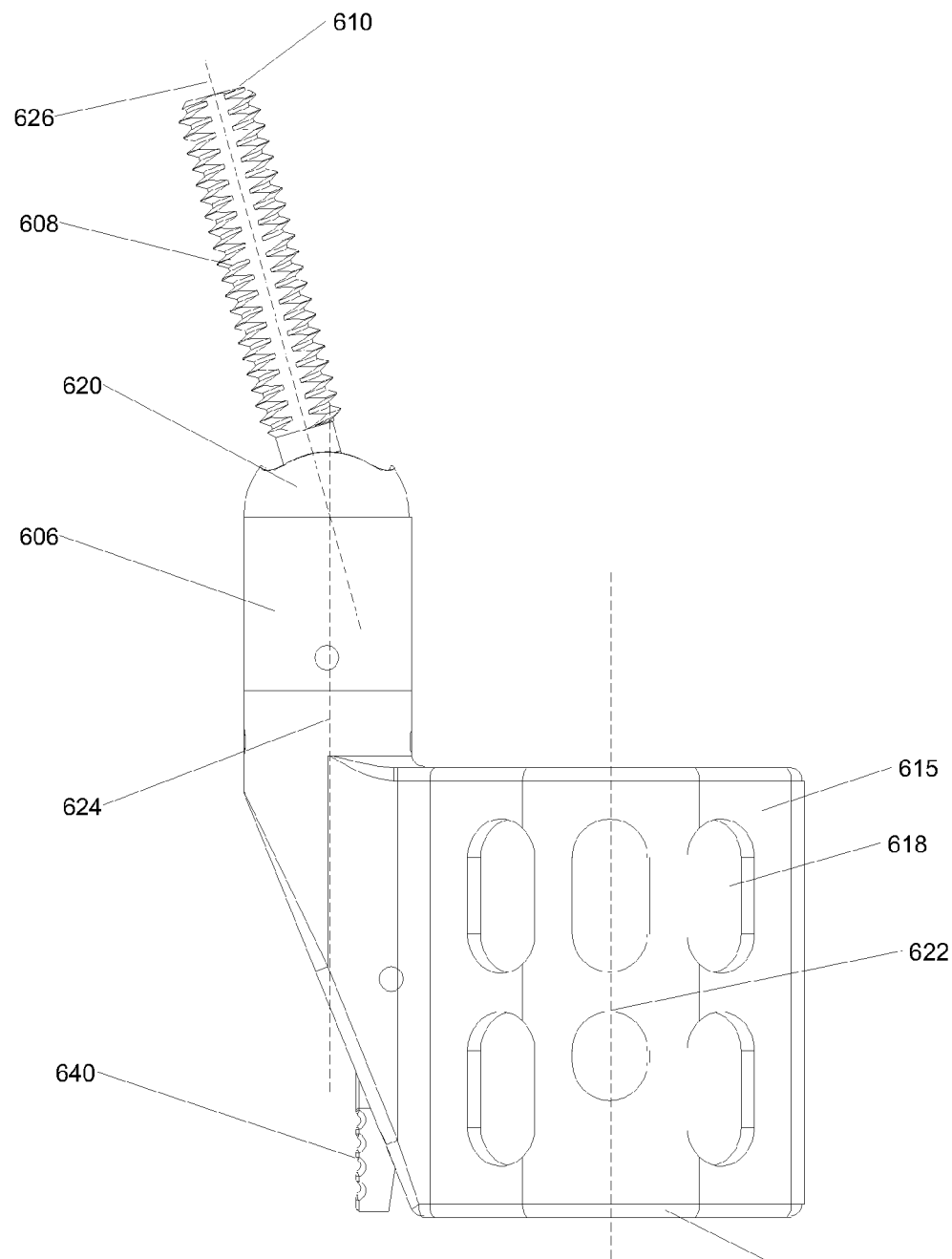
FIG. 9 includes an illustration of a plan view of an adapter.

As illustrated in FIG. 9, the adapter 600 may have a lumen axis 622, an intermediate axis 624, and a bolt axis 626. In the illustrated example, the lumen axis 622 and the intermediate axis 624 may be parallel. Alternatively, the intermediate axis 624 may be skewed relative to the lumen axis 622. Further, the bolt axis 626 may intersect the intermediate axis 624 at the ball joint 620 and may pivot such that the bolt axis 626 may or may not be parallel to the intermediate axis 624.

Figure 10:
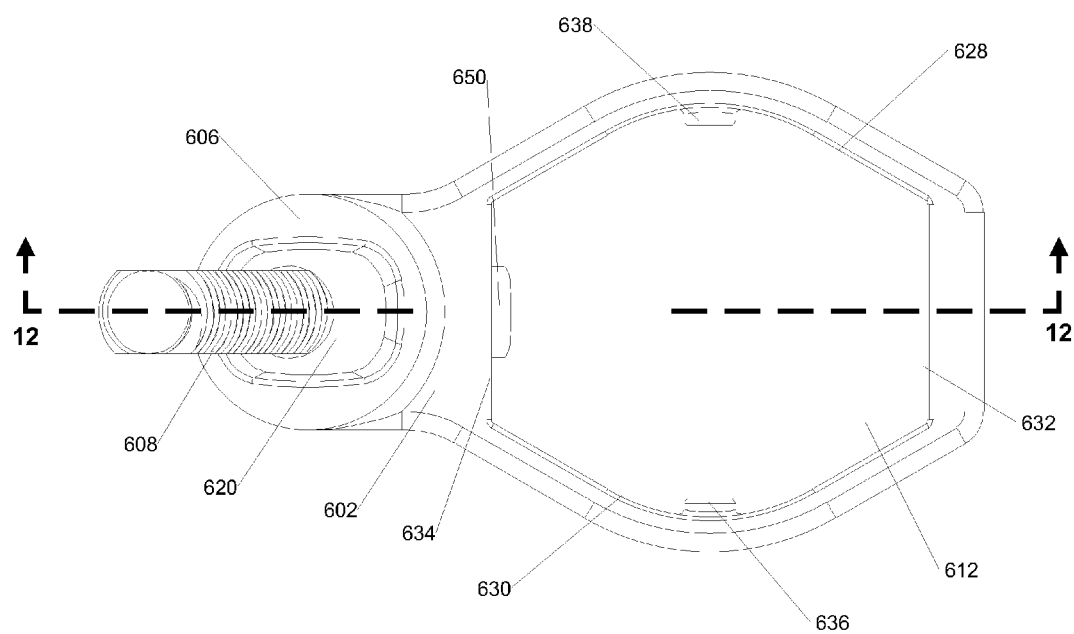
FIG. 10 includes an illustration of a top plan view of an adapter.
Figure 11:
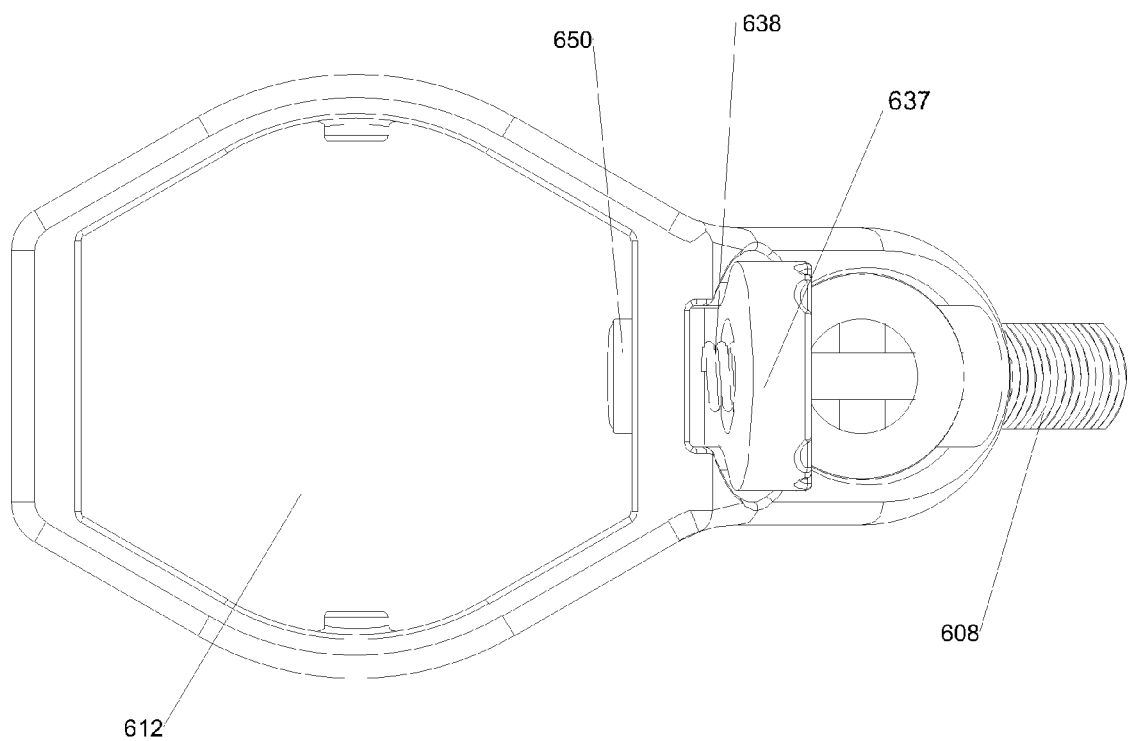
FIG. 11 includes an illustration of a bottom plan view of an adapter.
Figure 12:
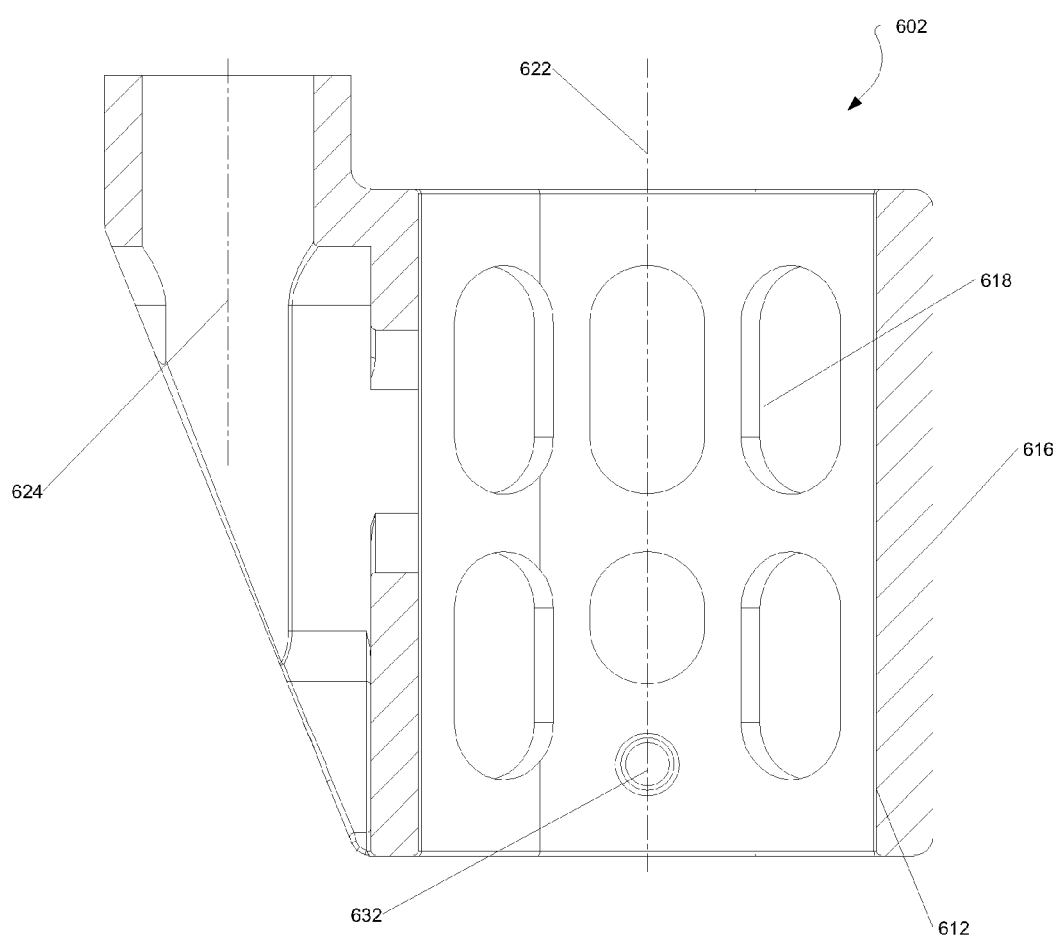
FIG. 12 includes an illustration of a cross section view of an adapter taken along line 12-12 of FIG. 10.
Figure 13:
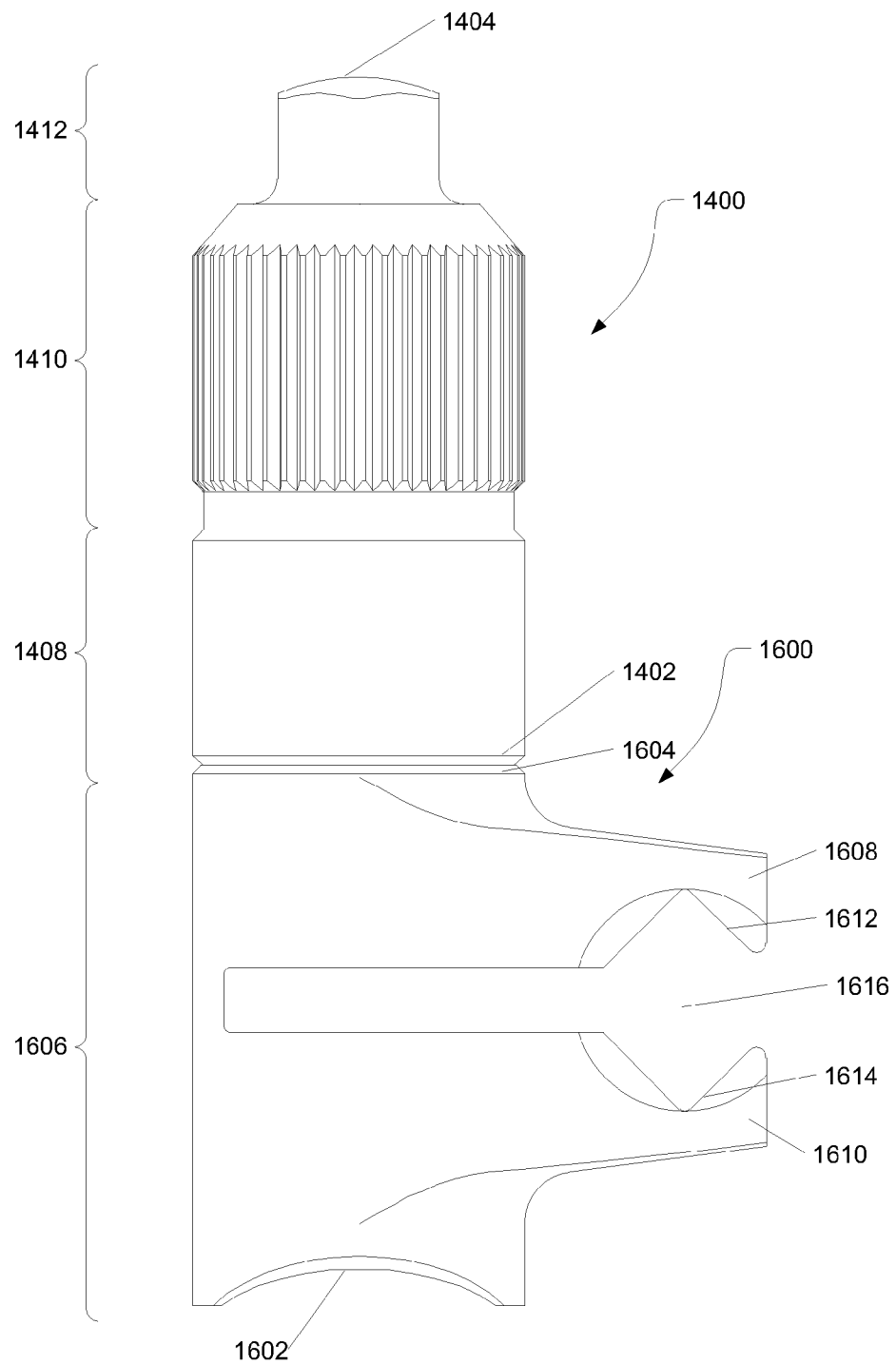
FIG. 13 includes an illustration of a side plan view of a holder and a nut.

As illustrated in FIG. 10, the lumen 612 may be non-circular and may have arcuate portions 628, 630 and linear portions 632, 634. The lumen 612 may have nubs 636, 638 configured to interact with indentations 706 of the pedicle post 700. As illustrated in FIG. 11 and FIG. 12, the nub 636 may be within the lumen 612 near the proximal end 604 and aligned with the lumen axis 622.

Additionally, a quick release connector may engage and hold the pedicle post 700 in place. For example, the quick release connector may include a release button 637 attached to the cage 616 of the coupling portion 602. As illustrated in FIG. 11, the push button release 637 has a nodule 650 extending into the lumen 612 to releasably engage a pedicle post 700. The push button release 637 includes a spring 638 to bias the push button release 637 into an engaged position, and force applied to the finger contact area 640, illustrated in FIG. 8, biases the push button release 637 against the spring 638, withdrawing the nodule 650 from the lumen 612 of the coupling portion 602 and releasing a connected pedicle post 700.

Description of the Holder and Second Connector

Figure 14:
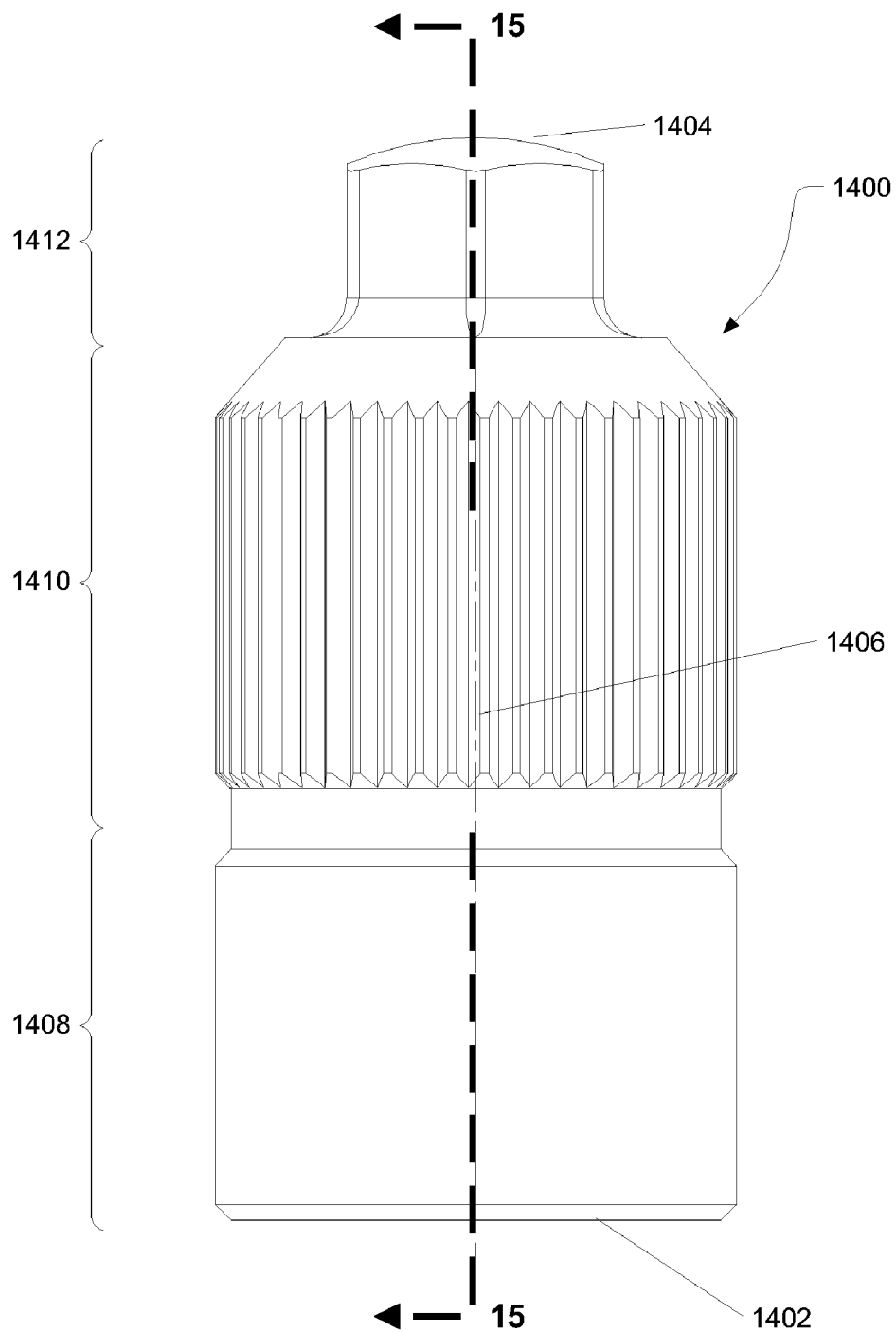
FIG. 14 includes an illustration of a plan view of a nut.

Referring to FIGS. 13 to 21, a holder 1600 and a second connector, such as a nut 1400, are illustrated. While the second connector is generally depicted as a nut in the illustrated embodiment, alternative embodiments are envisaged that may engage alternative types of connectors used in conjunction with the bolt 608. As illustrated in FIG. 14, the nut 1400 may have a proximal end 1402, a distal end 1404, and a nut axis 1406. Starting at the proximal end 1402, the nut 1400 may include a holder contacting portion 1408, a knurled portion 1410, and a tool engaging portion 1412. The knurled portion 1410 may have a diamond pattern, a series of straight ridges, or a helical pattern. In general, the knurled pattern may provide a better grip than a smooth surface. The tool engaging portion 1412 may be shaped to engage a tool. For example, the tool engaging portion 1412 may have a square, hexagonal, or octagonal cross section adapted to engage a tool such as a nut driver or a wrench.

Figure 15:
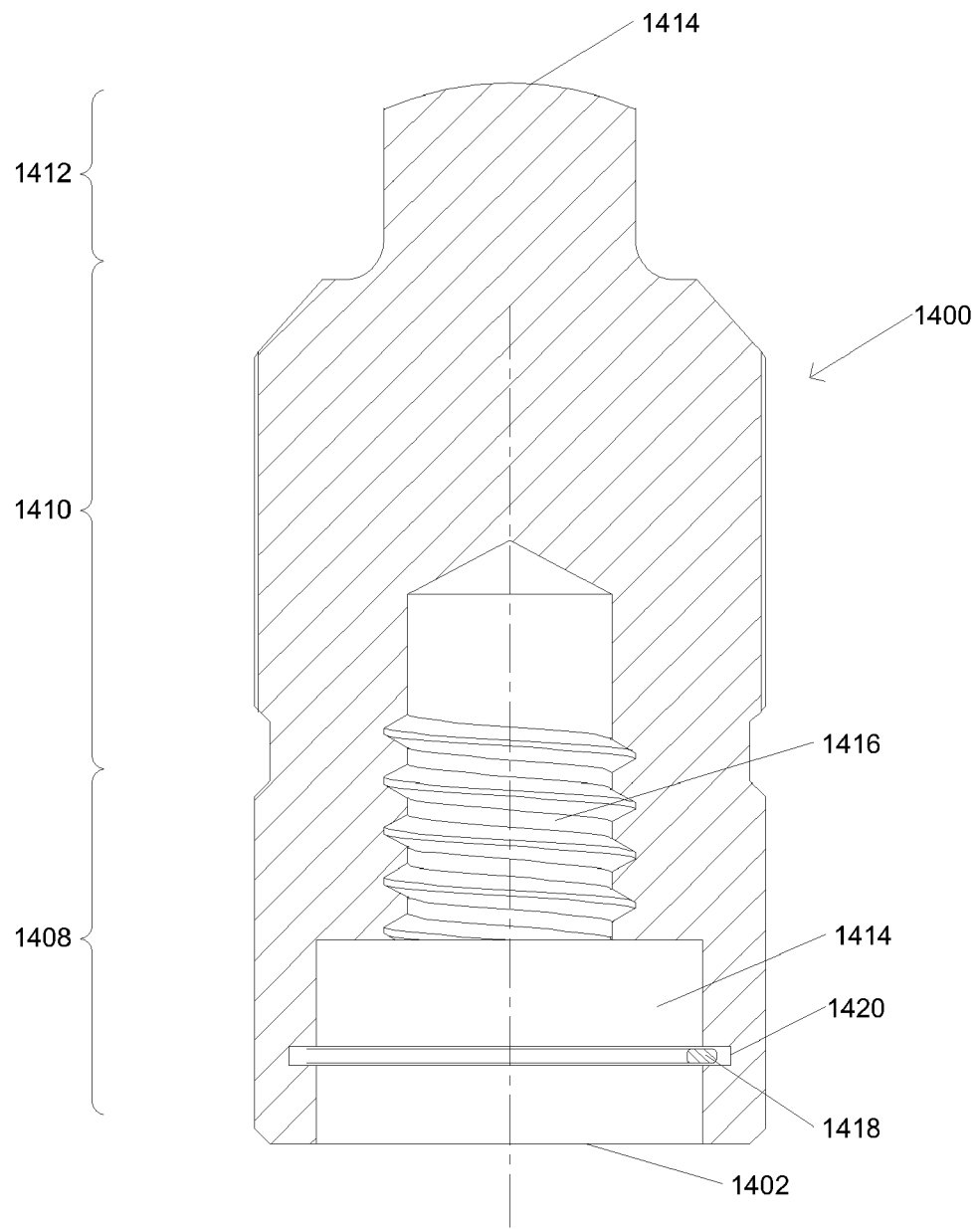
FIG. 15 is a cross-section view of a nut taken along line 15-15 of FIG. 14.

As illustrated in FIG. 15, the nut 1400 may included a holder engaging lumen 1414 at the proximal end 1402, and a threaded lumen 1416 extending into the knurled region 1410. The threaded lumen 1406 may engage the bolt 608 of the adapter 600.

Figure 16:
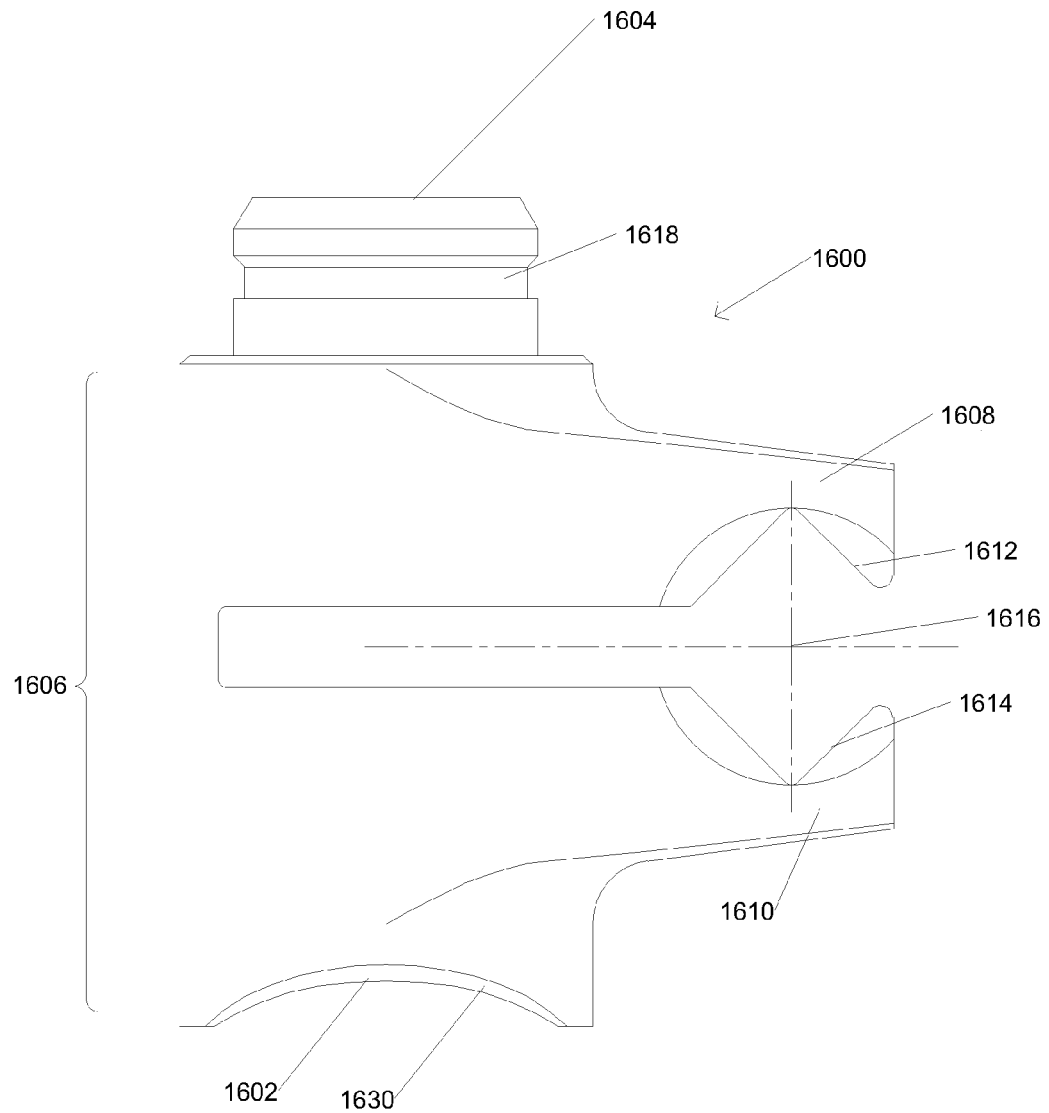
FIG. 16 includes an illustration of a side plan view of a holder.
Figure 17:
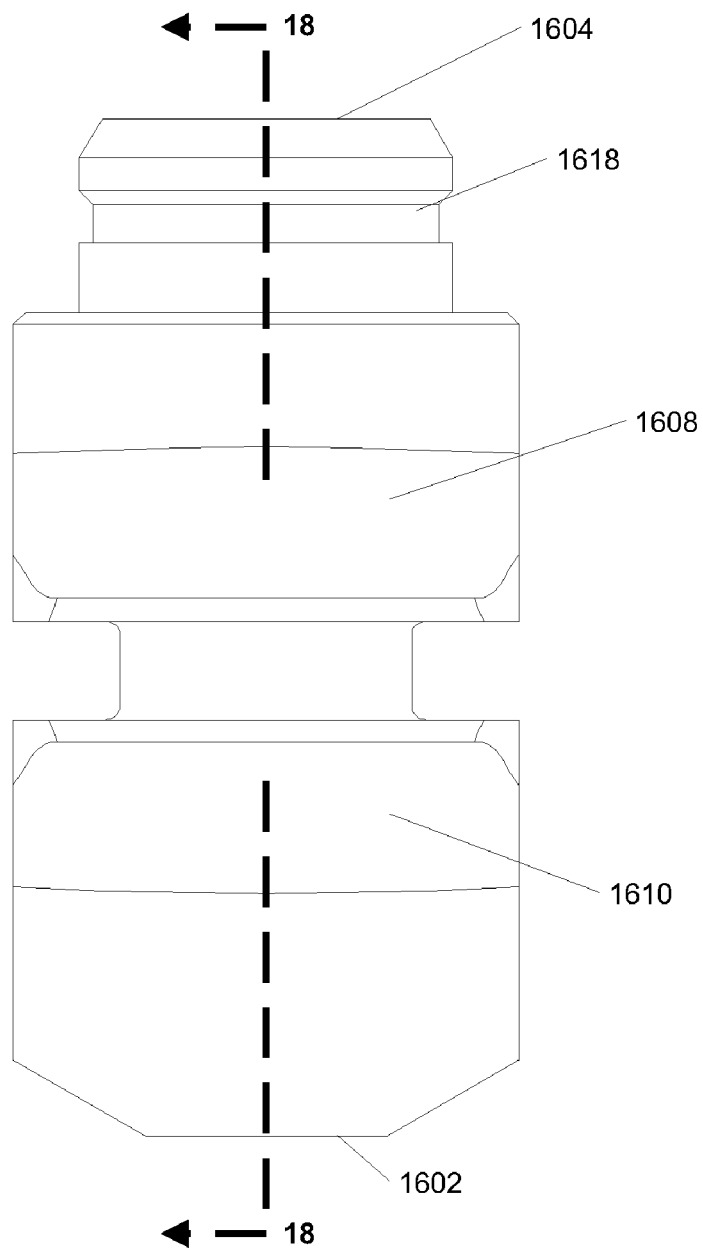
FIG. 17 includes an illustration of a front plan view of a holder.

As illustrated in FIG. 16, the holder 1600 may include a body 1606 having a proximal end 1602 and a distal end 1604. An upper arm 1608 and a lower arm 1610 may extend from the body 1606. The upper arm 1608 may include an upper seat 1612 and the lower arm 1610 may include a lower seat 1614. A rod engagement region 1616 may be defined between the upper seat 1612 and the lower seat 1614. At the distal end 1604, the body 1606 may include a nut-contacting region 1618.

Figure 18:
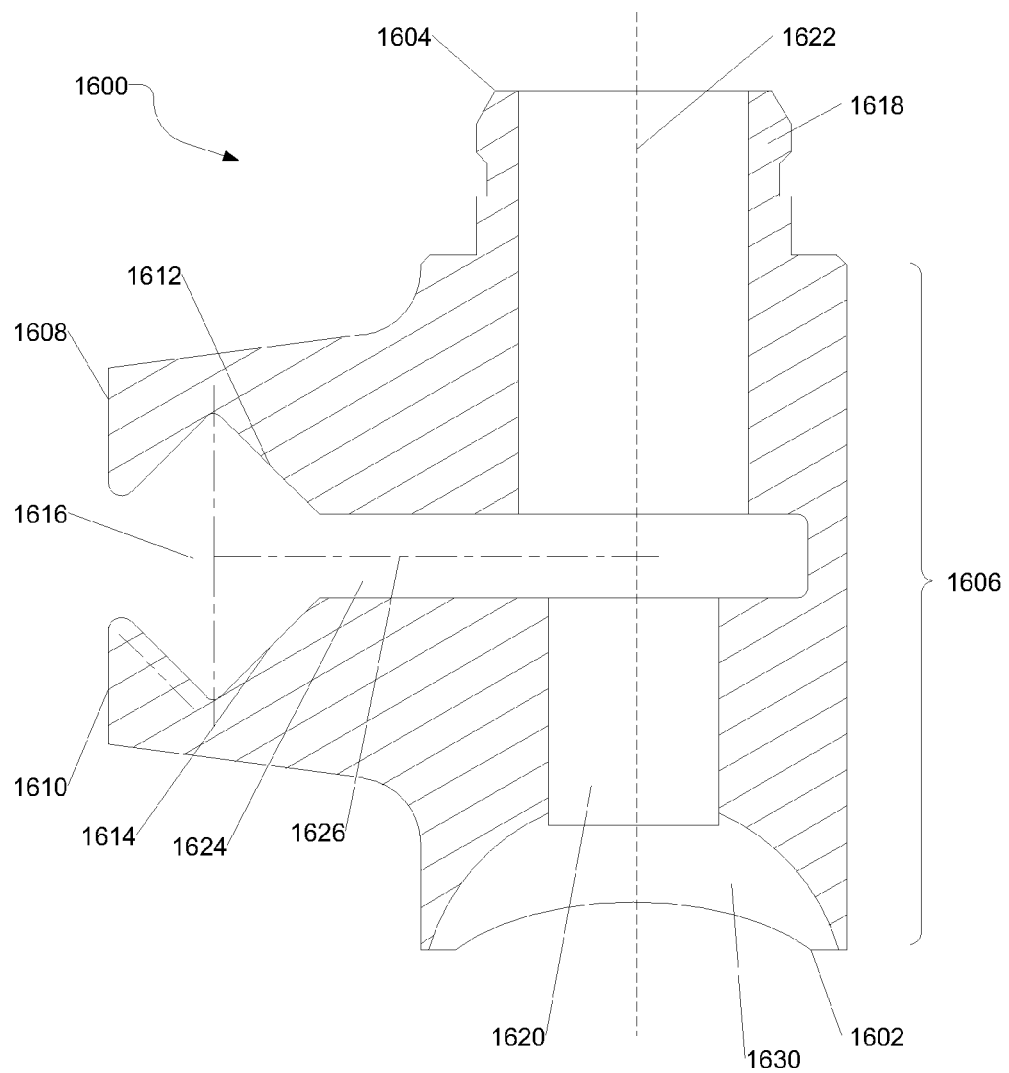
FIG. 18 includes an illustration of a cross-section view of a nut taken along line 18-18 of FIG. 17.
Figure 19:
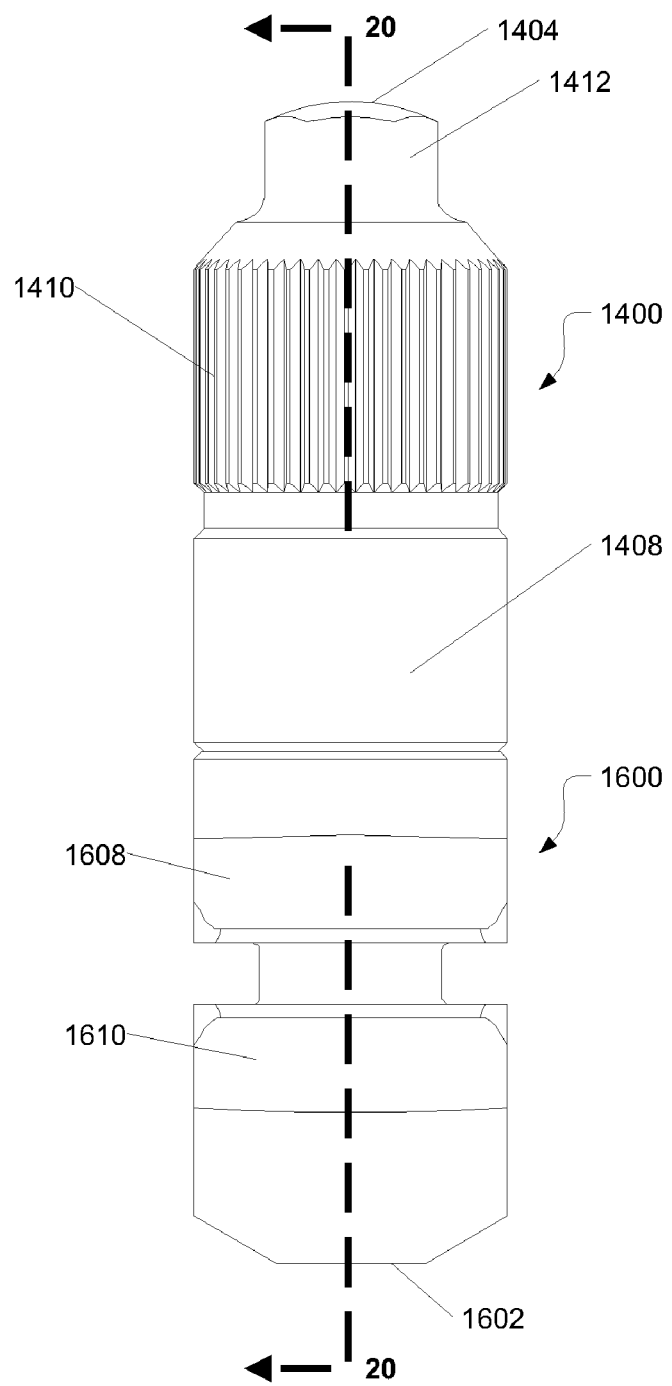
FIG. 19 includes an illustration of a front plan view of a nut and a holder.

As illustrated in FIG. 18, the holder 1600 may include a lumen 1620 extending through the body 1608 from the proximal end 1602 to the distal end 1604. The lumen 1620 may have a central axis 1622. The holder 1600 may also include a slot 1624 between the upper arm 1608 and the lower arm 1610. The slot 1624 may extend from the rod engagement region 1628 into the body 1606, intersecting the lumen 1620. In a particular example, a slot axis 1626 may be perpendicular to the central axis 1622 of the lumen 1620.

In addition, the body 1606 may include a concave receiving surface 1630 at a proximal end 1602. For example, the concave receiving surface 1630 may be configured to contact the ball and socket joint 1620 of the bolt 608 and the intermediate portion 606 of the adapter 600 and permit rotational movement with respect to at least one axis relative to the adapter 600. In an example, by virtue of the concave receiving surface 1630 of the body 1606, the holder 1600 may be rotationally moveable with respect to the adapter 600, such as along one or more axes.

Figure 20:
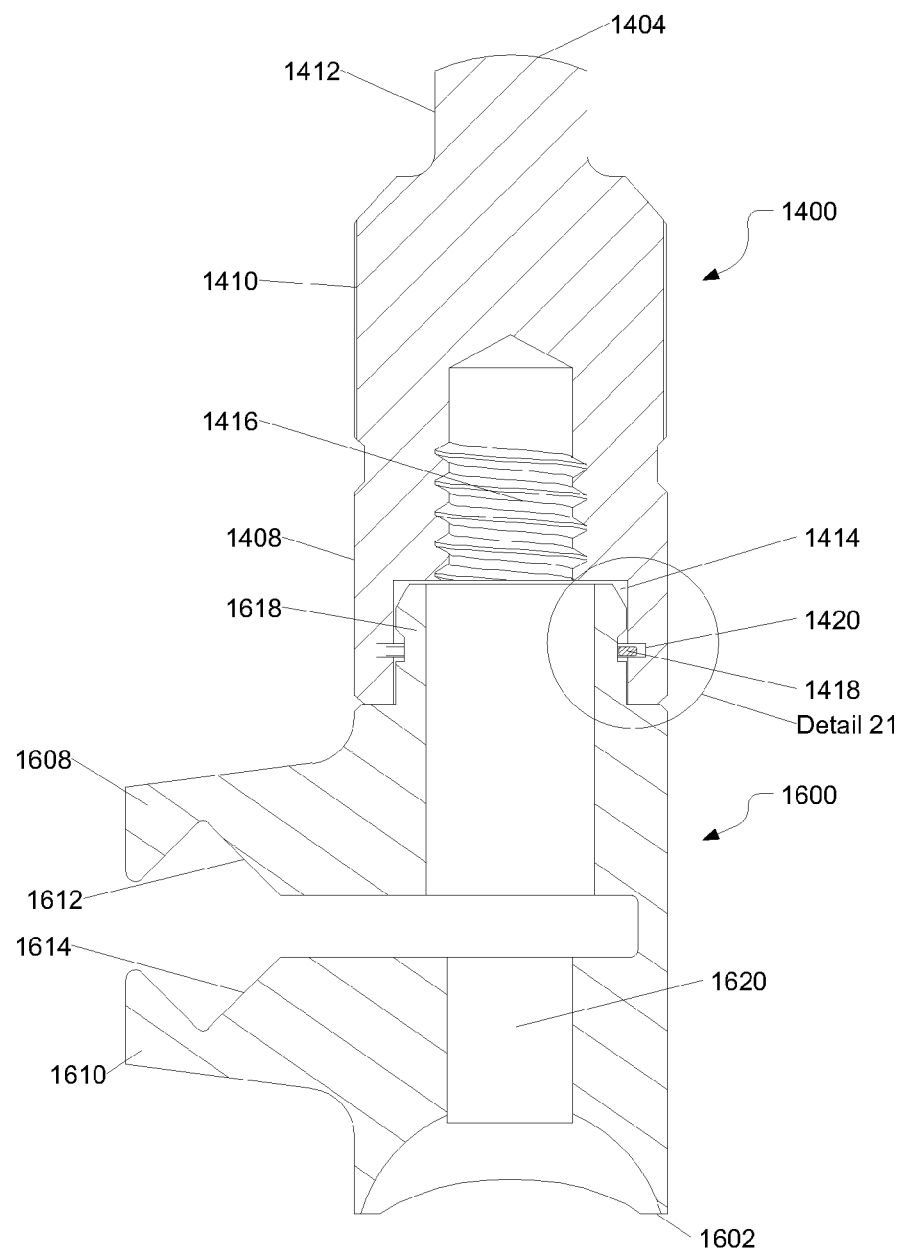
FIG. 20 includes an illustration of a cross-section view of a nut and a holder taken along line 20-20 of FIG. 19.
Figure 21:
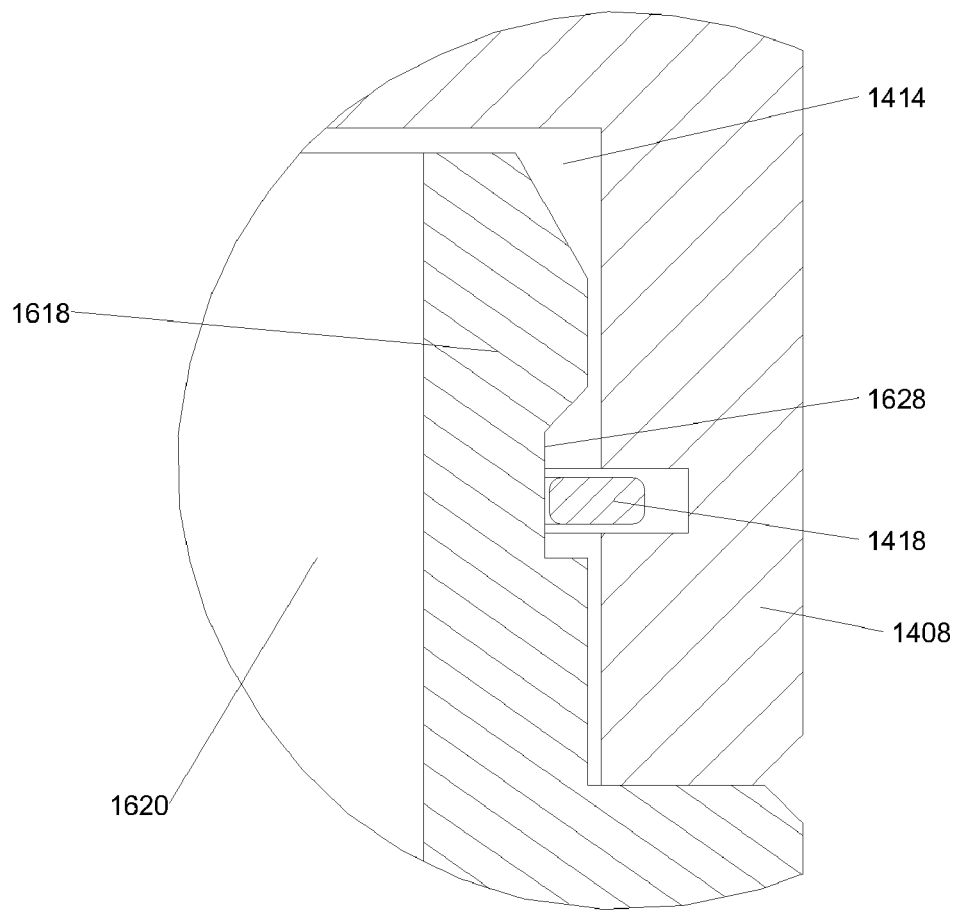
FIG. 21 includes an illustration of a detail view of Detail 21 of FIG. 20.

As illustrated in FIG. 20, the nut-contacting region 1618 of the holder 1600 may engage the holder engaging lumen 1414 of the nut 1400. The nut 1400 may include a holder engaging ring 1418 engage with a grove 1420 within the holder engaging lumen 1414. Illustrated in detail in FIG. 21, the holder engaging ring 1418 may also engage a channel 1628 of the nut-contacting region 1618, securing the nut 1400 to the holder 1600, while permitting the nut 1400 to rotate around the central axis 1622 of the holder 1600.

Returning to FIG. 20, when the nut 1400 and holder 1600 are engaged, the lumen 1618 of the holder 1600 aligns with the threaded lumen 1414 of the nut 1400. The bolt 608 of the adapter 600 may extend through the lumen 1618 of the holder 1600 and threadably engage the threaded lumen 1414 of the nut 1400. Engagement of the bolt 608 by the nut 1400 may cause compressive force on the holder 1600 and, in particular, on the arms 1608 and 1610, moving the arms 1608 and 1610 closer together and potentially fixing a rod between the upper seat 1612 and the lower seat 1614.

Description of a Multipoint Correction System

In particular, the adapter 600, the nut 1400, and the holder 1600 may be used to couple a pedicle attachment system to a multipoint corrective system for correcting spinal curvature. For example, a plurality of pedicle posts 700 may be secured to a plurality of vertebrae. A plurality of adapters 600 may be coupled to the pedicle posts 700, each of the pedicle posts 700 coupled to one of the adapters 600. The adapters 600 may be coupled to the multipoint correction system using the holder 1600 and the nut 1400.

Figure 22:
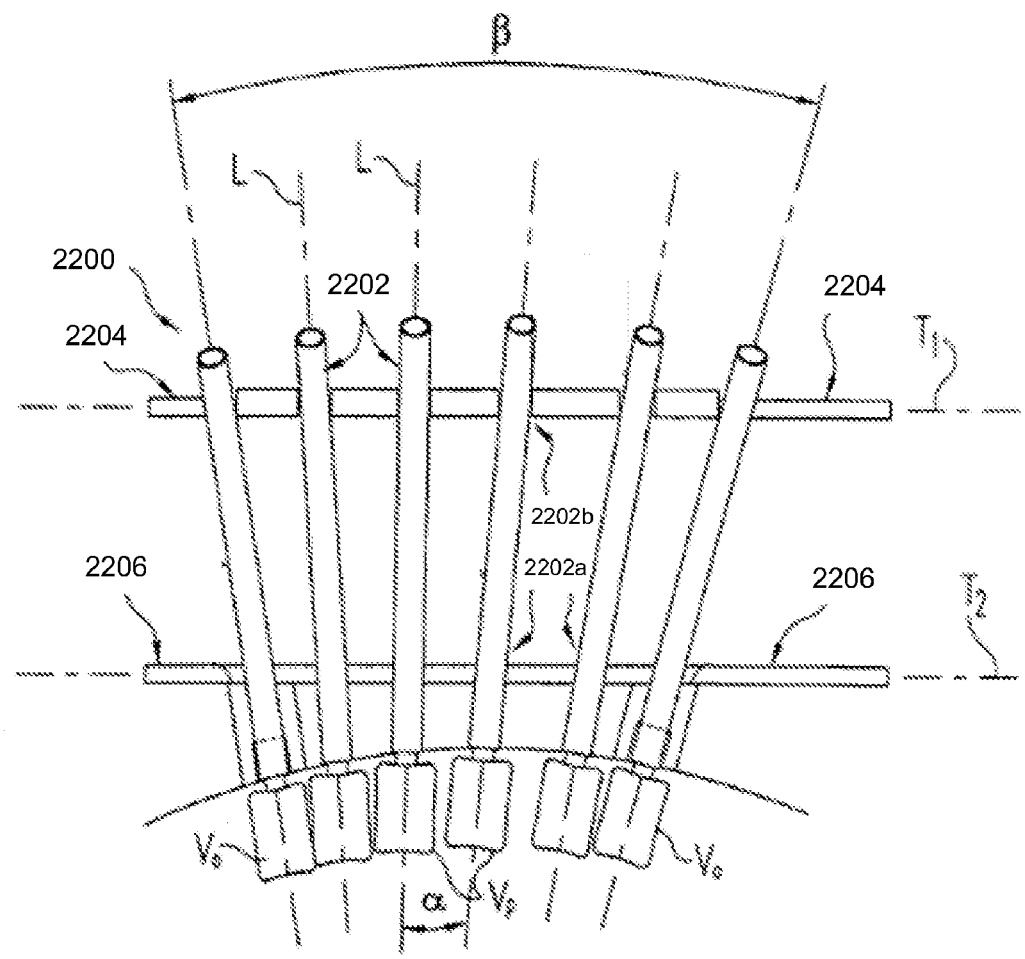
FIG. 22 includes an illustration of a plan view of a multipoint correction system.

To illustrate the general principle, FIG. 22 includes an illustration of a multipoint correction system 2200. The multipoint correction system 2200 may be used in treatment of the spinal column, and more particularly to reduce a spinal deformity. The multipoint correction system 2200 may be used to treat abnormal curvatures of the spinal column, such as, for example, scoliosis. Alternatively, the multipoint correction system 2200 may be used to treat other spinal deformities, including kyphotic deformities and other abnormal spinal curvatures.

The multipoint correction system 2200 may be configured to reposition or realign the vertebrae along one or more spatial planes toward their normal physiological position and orientation. Preferably, the spinal deformity may be reduced systematically in all three spatial planes of the spine, thereby tending to reduce surgical times and provide improved results.

In an embodiment, the multipoint correction system 2200 generally includes a plurality of coplanar rods 2202 adapted for coupling to a number of vertebrae, a first transverse rod 2204 extending between and engaged with the coplanar rods 2202, a second transverse rod 2206 extending between and engaged with the coplanar rods 2202.

The coplanar rods 2202 each extend generally along a longitudinal axis L and include a proximal portion 2202a and an opposite distal portion 2202b. The first transverse rod 2204 extends generally along a first transverse axis $T_1$ and is engaged with the coplanar rods 2202, and the second transverse rod 2206 extends generally along a second transverse axis $T_2$ and is likewise engaged with the coplanar rods 2202. The first transverse rod 2204 is engaged with the distal portions 2202b of the coplanar rods 2202 to maintain the distal portions 2202b in general alignment along the first transverse axis $T_1$. The second transverse rod 2206 is axially displaced along the coplanar rods 2202 in a proximal direction from a position adjacent the distal portions 2202b toward the proximal portion 2202a, which in turn results in positioning of the proximal portions 2202a in general alignment along the second transverse axis $T_2$. The coplanar rods 2202 act on the vertebrae to reduce the spinal deformity via both translational and rotational movement of the vertebrae, wherein the anteroposterior axes A-P of the vertebrae are transitioned from an abnormal or non-coplanar state toward a corrected or coplanar state wherein the anteroposterior axes A-P of the vertebrae are positioned substantially within a common plane P, such as the sagittal plane.

Figure 23:
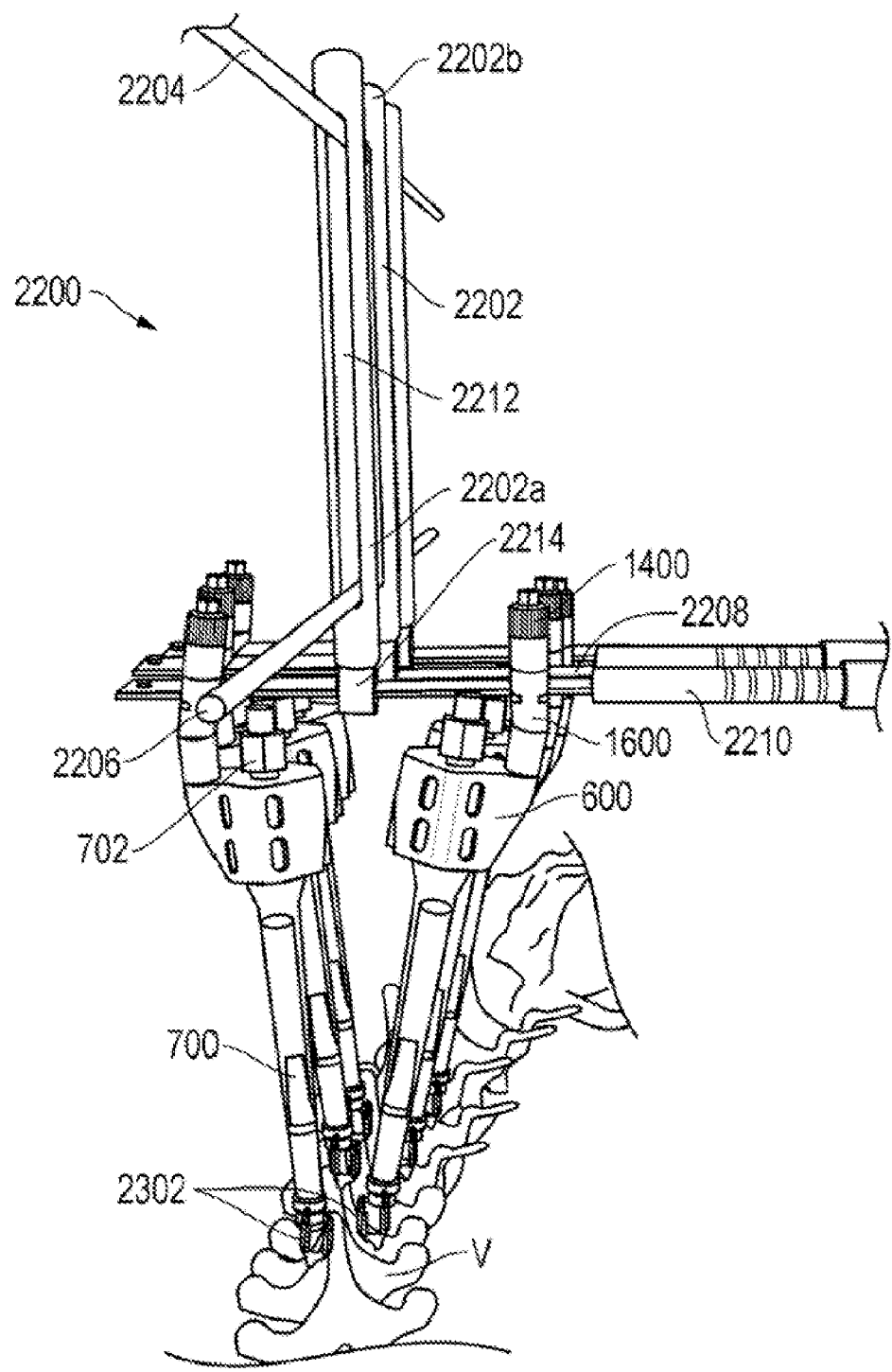
FIG. 23 includes an illustration of a perspective view of a spinal correction system.

In a particular embodiment, FIG. 23 illustrates the pedicle posts 700 coupled to the multipoint correction system 2200 via the adapter 600. In the illustrated embodiment, two pedicle screws 2302 may be inserted into each vertebra. Pedicle posts 700 may be attached to each of the pedicle screws 2302 and the adapters 600 may be attached to the heads 702 of the pedicle posts 700. The nuts 1400 and holders 1600 may be threaded onto the bolts of the adapters 600 and coronal rods 2208 may be fixedly coupled to the holders 1600. In particular, each coronal rod 2208 may extend between the holders 1600 coupled through the adapters 600 to the pedicle post 700 associated with a single vertebra. For example, a vertebra has two pedicles. A pedicle post 700 may be attached to each pedicle and may coupled via the adapter 600 to a holder 1600. A coronal rod 2208 may extend between the two holders 1600 associated with the vertebra. In a particular example, the coronal rods 2208 may include a handle 2210 to assist with insertion between the arms of the holders 1600.

In an embodiment, the coplanar rods 2202 may be attached to the coronal rods 2208. The coplanar rods may include a coupling 2214 for attachment to the coronal rods and may include a longitudinal slot 2212. For example, the coplanar rods 2202 may extend perpendicular to the coronal rods 2208 and may be positioned between the holders 1600 securing each rod 2208. A first transverse rod 2204 may be inserted through the distal portions 2202b of the coplanar rods 2202, and a second transverse rod 2206 may be positioned through the proximal portions 2202a of the coplanar rods 2202.

Description of a Method of Treating a Spine

Figure 24:
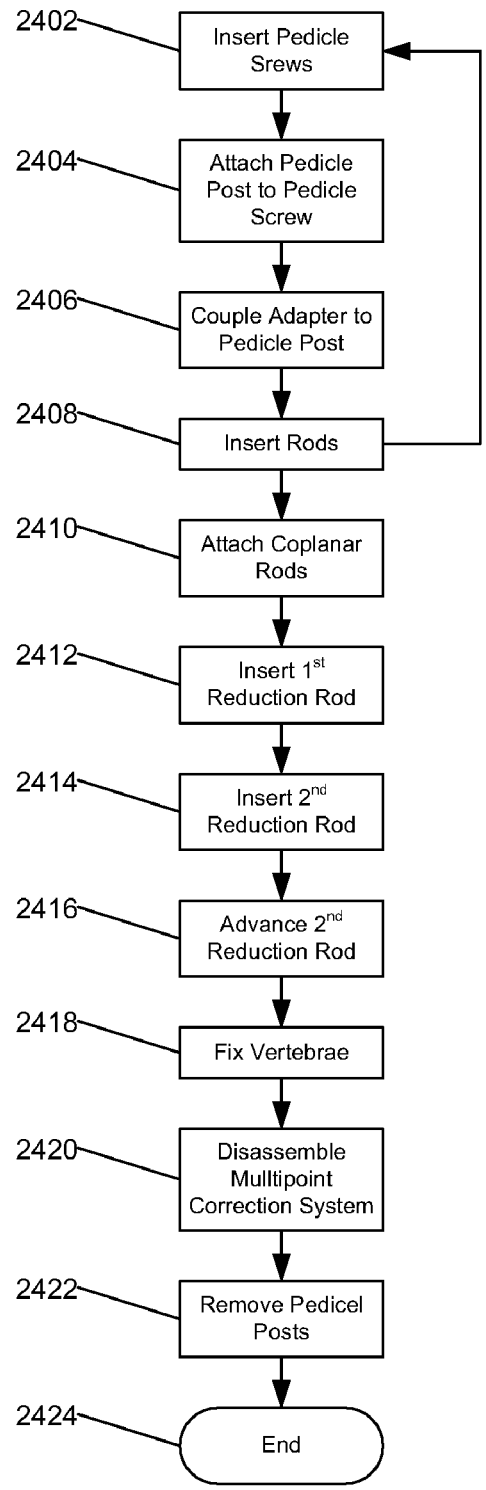
FIG. 24 includes an illustration of method of treating a spinal deformity.

Referring to FIG. 24, a method of treating a spine is illustrated. As illustrated at 2402, a pedicle screw may be inserted into a pedicle of a vertebra. For example, the pedicle screw may be inserted through a small incision in the back. Typically, a small incision is made in a position overlying the pedicle of a vertebra, an indentation is tapped into the pedicle, and the pedicle screw is driven into indentation in the pedicle. In an example, a guidewire may be used to position and orient the pedicle screw as it is driven into the pedicle. Alternatively, the pedicle screw may be driven into the pedicle absent a guide wire.

As illustrated at 2404, a pedicle post may be attached to the pedicle screw. The pedicle post may act as an extension to manipulate the vertebrae from a point external to the body. In particular, the pedicle post may establish a lever arm that may be used to manipulate the orientation and position of the vertebra. Further, two pedicle posts attached to a vertebra may establish two lever arms that may be manipulated relative to each other to alter the orientation of the vertebra relative spinal planes.

As illustrated at 2406, an adapter may be coupled to the pedicle post, and the adapter may be connected to the coronal rods, as illustrated at 2408. For example, the adapter may be coupled to a distal end of the pedicle post using a quick release connection. In particular, the adapter may secure the pedicle post, limiting relative movement of the adapter relative to the pedicle post, for example, in axial and rotational directions. Further, a holder and nut may be threaded onto a bolt of the adapter and may be tightened to fixedly couple the coronal rods, each associated with a single vertebra In an example, steps, as illustrated at 2402 through 2408, may be repeated so that multiple vertebrae may be manipulated. For example, a surgeon may insert multiple pedicle screws in multiple vertebrae, followed by attaching multiple pedicle posts to the multiple pedicle screws. Alternatively, the surgeon may perform steps, as illustrated at 2402 through 2408, on a vertebra and then repeat steps, as illustrated at 2402 through 2408, with another vertebra.

As illustrated at 2410, coplanar rods may be attached to the coronal rods. The coplanar rods may not be aligned in a spine with an abnormal curvature. In particular, the coplanar rods extend perpendicular to the coronal rods. As illustrated at 2412, a first transverse rod may be inserted through the slots 2212 in the coplanar rods. The alignment of the vertebrae may be manipulated until the coplanar rods are aligned sufficiently to insert the first transverse rod through the distal ends of the coplanar rods.

A second transverse rod may be inserted through the distal ends of the coplanar rods, as illustrated at 2414. In a particular example, the second transverse rod may be inserted just below the first transverse rod through the coplanar rods. As illustrated at 2416, the second transverse rod may be advanced along an axial channel within the coplanar rods towards the proximal end of the coplanar rods. Advancement of the second transverse rod toward the spine forces alignment of the coplanar rods and acts to correct the curvature of the spine. As illustrated at 2418, the vertebrae are fixed in place, such as by placing a fixing element through the pedicle screws. In an example, the fixing element may be a rod or beam to rigidly secure the relative position of the aligned vertebrae. Alternatively, the fixing element may be a wire or tether, which permits some relative movement of the vertebrae.

Following the insertion of the fixing element, the multipoint correction system may be disassembled and removed from the pedicle posts, as illustrated at 2420. Further, as illustrated at 2422, the pedicle posts may be removed from the pedicle screws. The method may end, as illustrated at 2424, with the repositioning of tissues and closing of the surgical site.

Figure 25:
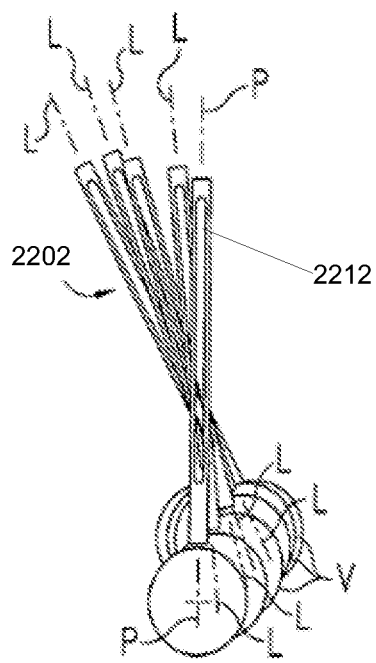
FIG. 25, FIG. 26, FIG. 27, FIG. 28, FIG. 29, and FIG. 30 include schematical illustrations of a scoliotic spine and correction system in various stages of alignment.

To further illustrate the general procedure, FIGS. 25 though 30 include schematic illustrations of the process steps 2410 through 2416 of FIG. 24. For simplicity, the coplanar rods 2202 are illustrated as directly attaching to the vertebrae. However, the coplanar rods 2202 may be coupled to the vertebrae through a spinal correction system including pedicle posts 700, adapters 600, holders 1600, and coronal rods 2208 as previously described.

For example, FIG. 25, corresponding to 2410 of FIG. 24, illustrates misalignment of the coplanar rods 2202 in a spine with abnormal curvature. As discussed above with regard to FIGS. 4 and 5, in a scoliotic spine, the natural physiological position and alignment of the vertebrae are altered due to abnormal vertebral rotation and translation. As a result, the anteroposterior axes of the vertebrae, which are normally positioned within a common plane (i.e., the sagittal plane), extend along multiple planes in a non-coplanar state. Additionally, in a scoliotic spine, the thoracic region of the spine is typically lordotic, thereby resulting in divergence between the anteroposterior axes.

Referring once again to FIG. 25, the coplanar rods 2202 are initially positioned and arranged such that the longitudinal axes of the coplanar rods 2202 are in substantial co-axial alignment with the uncorrected anteroposterior axes of the vertebrae. As a result, the longitudinal axes L of the coplanar rods 2202 are initially not in alignment with one another along a common plane P, but instead extend along multiple planes in a non-coplanar configuration.

Figure 26:
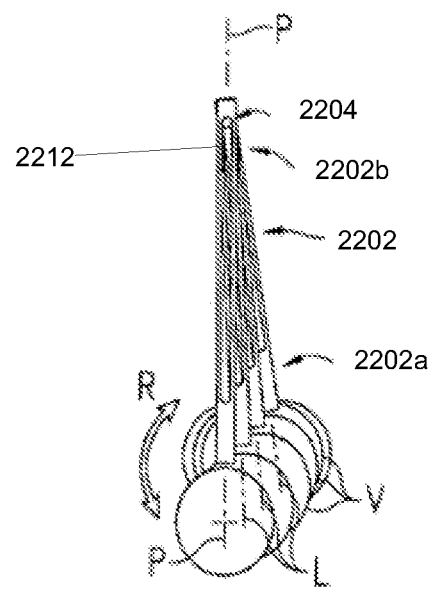

As illustrated in FIG. 26, corresponding to 2412 of FIG. 24, the distal portions 2202b of the coplanar rods 2202 are drawn together in general alignment with one another and the first transverse rod 2204 is inserted through the distal end portions of each of the slots 2212 in the coplanar rods 2202. In order to facilitate alignment of the distal portions 2202b with one another, the coplanar rods 2202 may be manually grasped and manipulated by the surgeon or an instrument or tool may be used to exert a lateral or torsional force onto one or more of the coplanar rods 2202. However, in another embodiment, general alignment of the distal portions 2202b with one another may be accomplished by inserting the transverse rod 2204 into central portions of the slots 2212, which may initially be in closer alignment with one another compared to the proximal end portions of the slots 2212. Once inserted into the central portions of the slots 2212, the first transverse rod 2204 may be axially displaced through the slots 2212 in a distal direction, which in turn draws the distal portions 2202b of the coplanar rods 2202 into general alignment with one another via the exertion of lateral forces onto the inner side surfaces of the coplanar rods 2202 which define the slots 2212. Various instruments may be used to facilitate axial displacement of the first transverse rod 2204 through the slots 2212, the likes of which will be discussed in greater detail below with regard to the second transverse rod 2206. Initial introduction of the first transverse rod 2204 into the slots 2212 may be facilitated via the use of a surgical mallet, a slap hammer, or by any other suitable tool or instrument.

In general, the first transverse rod 2204 cooperates with the coplanar rods 2202 to maintain alignment of the distal portion 2202b generally along the first transverse axis $T_1$ (see FIG. 22), with the first transverse axis $T_1$ preferably extending along the sagittal plane P. Alignment of the distal portions 2202b of the coplanar rods 2202 generally along the first transverse axis $T_1$ correspondingly imparts rotational movement to one or more of the coplanar rods 2202. Rotation of the coplanar rods 2202 in turn imparts a rotational force onto the corresponding vertebrae to derotate the vertebrae generally along the transverse plane in the direction of arrow R. The direction of derotation is dependent on the particular characteristics of the spinal deformity being treated, and may occur in a clockwise direction or a counter-clockwise direction. Further, bringing the distal portions 2202b into general alignment with one another may not result in rotation of one or more of the coplanar rods 2202, in which case the corresponding vertebrae will not be rotationally affected. Although alignment of the distal portions 2202b of the coplanar rods 2202 partially reduces the spinal deformity, further correction may be utilized.

Figure 27:
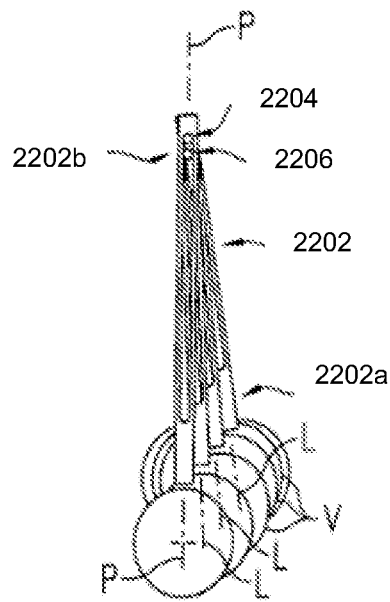

Referring to FIG. 27, corresponding to 2414 of FIG. 24, the second transverse rod 2206 may be inserted through the distal end portions of each of the slots 2212 in the coplanar rods 2202 adjacent the first transverse rod 2204. Since the distal end portions of the slots 2212 are maintained in general alignment with one another via the first transverse rod 2204, insertion of the second transverse rod 2206 into the slots 2212 may not significantly manipulate the coplanar rods 2202. However, introduction of the second transverse rod 2206 into the slots 2212 may be facilitated via the use of a surgical mallet, a slap hammer, or by any other suitable tool or instrument.

Figure 28:
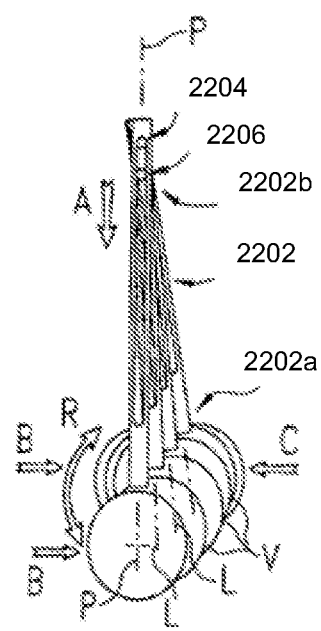
Figure 29:
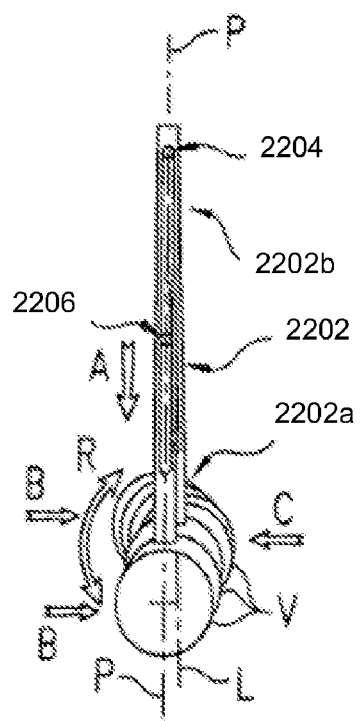
Figure 30:
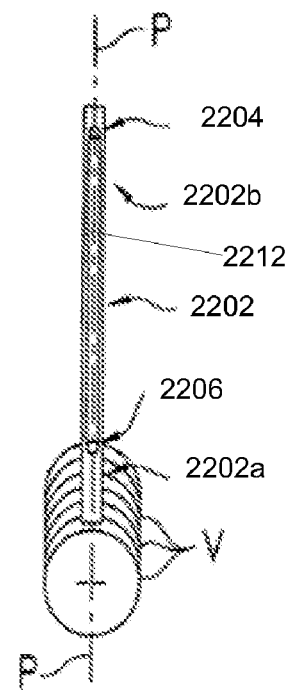

FIGS. 28 through 30 correspond to 2416 of FIG. 244. As illustrated in FIG. 28, with the first transverse rod 2204 remaining in a substantially stationary position to maintain the distal portions 2202b in general alignment with one another, the second transverse rod 2206 is proximally displaced through the slots 2212 in the coplanar rods 2202 in the direction of arrow A, away from the first transverse rod 2204 and generally along the plane P. Displacement of the second transverse rod 2206 through the slots 2212 may be facilitated via the use of a surgical mallet, a rod pusher or persuader, or a distracter device engaged between the second transverse rod 2206 and another element, such as the first transverse rod 2204, to distract the second transverse rod 2206 in a proximal direction away from the first transverse rod 2204. The tools or instruments used to displace the second transverse rod 2206 through the slots 2212 may be manually driven or may be powered. Additionally, the tools or instruments may be incrementally advanced in a controlled manner to provide incremental displacement of the second transverse rod 2206 through the slots 2212 in the coplanar rods 2202. Such incremental advancement may be provided by way of a rack-and-pinion type drive, a ratcheting drive, a turnbuckle mechanism, or by any other suitable drive or advancement mechanism.

Sliding engagement of the second transverse rod 2206 through the slots 2212 in turn draws the coplanar rods 2202 toward one another via the exertion of lateral forces onto the inner side surfaces of the slots 2212 of the coplanar rods 2202. Specifically, as the second transverse rod 2206 is proximally displaced through the slots 2212, one or more of the coplanar rods 2202 is correspondingly rotated about the first transverse rod 2204 toward the sagittal plane P. Rotation of the coplanar rods 2202 in turn imparts a rotational force onto the corresponding vertebrae to provide further derotation of the vertebrae generally along the transverse plane in the direction of arrow which, as discussed above, may occur in a clockwise direction or a counter-clockwise direction.

Additionally, sliding engagement of the second transverse rod 2206 through the slots 2212 (and rotation of the coplanar rods 2202 about the first transverse rod 2204) also imparts a lateral force onto the corresponding vertebrae, which in turn results in relative translational movement of the vertebrae generally along the coronal plane in the directions of arrow B or arrow C. The direction of translational movement of the vertebrae may be dependent on the particular spinal deformity being treated, and may occur in either or both of the directions of arrows B and C. Proximal displacement of the second transverse rod 2206 through the slots 2212 may not result in rotation of one or more of the coplanar rods 2202, in which case the corresponding vertebrae will not be rotationally or translationally affected. Derotation of the vertebrae in the direction of arrow R and translation of the vertebrae in the direction of arrows B and C results in a reduction of the misalignment of the vertebrae V along both the transverse and coronal planes.

Referring to FIG. 29, further proximal displacement of the second transverse rod 2206 through the slots 2212 in the coplanar rods 2202 results in additional derotation of the vertebrae generally along the transverse plane in the direction of arrow R, and additional translation movement of the vertebrae generally along the coronal in the directions of arrows B and C. Referring to FIG. 30, the second transverse rod 2206 is further displaced through the slots 2212 to a position adjacent the proximal portions 2202a of the coplanar rods 2202. In this position, the proximal portions 2202a are drawn into general alignment with one another along the second transverse axis $T_2$, with the second transverse axis $T_2$ preferably arranged and extending generally along the sagittal plane P. With the distal portions 2202b of the coplanar rods 2202 maintained in general alignment along the transverse axis $T_1$ via the first transverse rod 2204, and with the proximal portions 2202a drawn into general alignment with one another along the second transverse axis $T_2$ via displacement of the second transverse rod 2206, the longitudinal axes L of the coplanar rods 2202 are positioned in general alignment with one another in a co-planar relationship along the sagittal plane P. General alignment of the coplanar rods 2202 along the sagittal plane P in turn results in general alignment of the anteroposterior axes A-P of the vertebrae along the sagittal plane P, thereby reducing the spinal deformity via correcting misalignment of the vertebrae along both the coronal and transverse planes.

Description of a Surgical Kit

Figure 31:
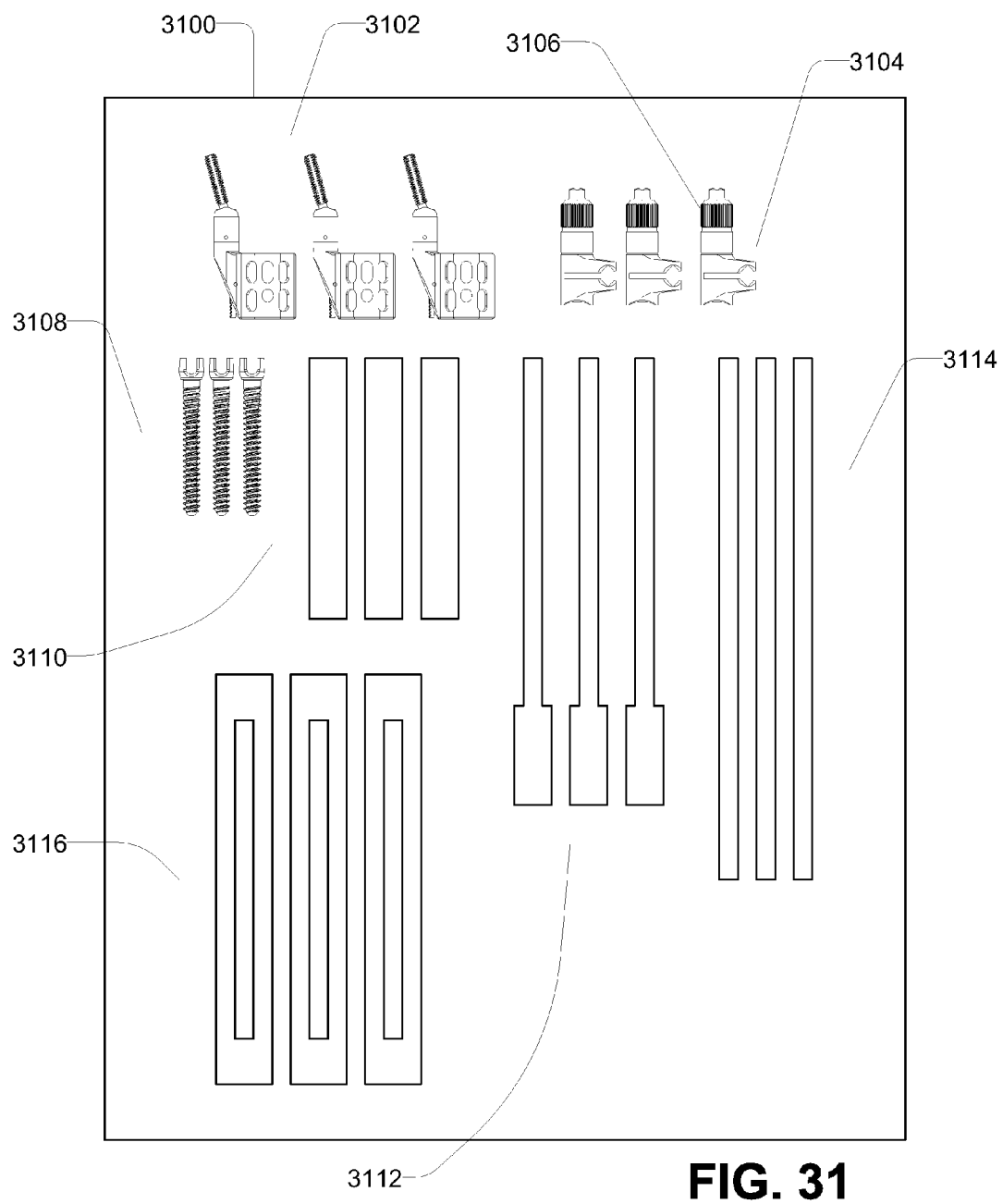
FIG. 31 includes an illustration of an exemplary surgical kit.

In an exemplary embodiment illustrated in FIG. 31, a surgical kit 3100 may include a set of adapters 3102, a set of holders 3104, and a set of nuts 3106. In addition, the kit 3100 may include a set of pedicle systems, including, for example, pedicle screws 3108 and pedicle posts 3110. Further, the surgical kit 3100 may include a set of coronal rods 3112, a set of coplanar rods 3114, a set of transverse rods 3116, or any combination thereof.

The surgical kit 3100 may be packaged and sterilized. For example, each component may be packaged and sterilized separately, in sets, or in any combination thereof. In particular, each of the components may be sterilizable via high temperature techniques, such as autoclaving. Further, each of the components may be sterilizable via chemical techniques, such as through ethylene oxide exposure, or irradiative techniques, such as gamma radiation techniques.

CONCLUSION

With the configuration of structure described above, the spinal correction system provides a device that may be used to treat a spine and substantially alleviate or minimize one or more symptoms associated with scoliotic spinal deformities.

In an exemplary embodiment, an adapter including a coupling portion defining a lumen to receive a pedicle post, an intermediate portion including a first end fixedly attached to a side of the coupling portion and including a second end distal from the coupling portion, and a bolt. A proximal end of the bolt is rotatably coupled to the second end of the intermediate portion and a distal end of the bolt includes a connector.

In a further exemplary embodiment, a spinal alignment system includes a plurality of pedicle assemblies and a multipoint alignment system. Each pedicle assembly of the plurality of assemblies includes a pedicle screw to engage a pedicle of a vertebra, a pedicle post to couple to the pedicle screw and provide mechanical torque to the vertebra, an adapter to couple to the pedicle post, a holder to couple to the adapter, and a nut rotationally coupled to the body of the holder at a second end. The adapter includes a coupling portion defining a lumen to receive the pedicle post, an intermediate portion including a first end fixedly attached to a side of the coupling portion and including a second end distal from the coupling portion, and a bolt. A proximal end of the bolt is rotatably coupled to the second end of the intermediate portion and a distal end of the bolt includes a threaded coupling. The holder has a body and two arms extending from the body. The body has first and second ends and defines a central lumen extending through the body from the first end to the second end. The central lumen receives the bolt at a first end. The bolt extends through the second end. The two arms define upper and lower seats to secure a rod. The nut defines a threaded lumen to receive the threaded end of the bolt. The multipoint alignment system is coupled to each holder of each pedicle assembly.

In an additional embodiment, a method of aligning at least two vertebrae includes applying a pedicle post to a pedicle screw implanted in a patient and securing an adapter to the pedicle post. The adapter includes a coupling portion defining a lumen to receive the pedicle post, an intermediate portion including a first end fixedly attached to a side of the coupling portion and including a second end distal from the coupling portion, and a bolt. A proximal end of the bolt is rotatably coupled to the second end of the intermediate portion and a distal end of the bolt includes a threaded coupling. The method further includes securing a holder to the adapter. The holder has a body and two arms extending from the body. The body has first and second ends and defines a central lumen extending through the body from the first end to the second end. The central lumen receives the bolt at a first end. The bolt extends through the second end. The two arms define upper and lower seats to secure a coronal rod. The method also includes securing the coronal rod of a multipoint alignment system to the holder.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. An adapter comprising:
   a coupling portion defining a lumen having a central axis to receive a pedicle post;
   an intermediate portion including a first end fixedly attached to a side of the coupling portion and including a second end distal from the coupling portion, and the intermediate portion is not co-axial with the central axis of the lumen;
   a bolt, a proximal end of the bolt is pivotally and rotatably coupled to the second end of the intermediate portion and a distal end of the bolt including a connector;
   a holder having a body and two arms extending from the body, the body having first and second ends and defining a central lumen extending through the body from the first end to the second end, the central lumen to receive the bolt at a first end, the bolt to extend through the second end, the two arms defining upper and lower seats to secure a coronal rod; and
   a second connector coupled to body at the second end, the second connector defining a lumen to receive the connector of the bolt.

2. The adapter of claim 1, wherein the connector is a threaded connector.

3. The adapter of claim 1, wherein the intermediate portion extending from the coupling portion substantially parallel to the central axis.

4. The adapter of claim 1, wherein the lumen of the coupling portion has a non-circular cross-section.

5. The adapter of claim 1, wherein the coupling portion is configured to be coupled to the pedicle post to prevent axial and rotational movement of the coupling portion relative to the pedicle post.

6. The adapter of claim 1, further comprising a release tab configured to releasably engage the pedicle post when a nodule of the release tab is within the lumen of the coupling portion.

7. The adapter of claim 1, wherein the proximal end of the bolt includes a ball joint, and wherein the second end of the intermediate portion defines a socket in which ball joint is located.

8. The adapter of claim 1, wherein the two arms of the holder pinch in response to connection of the second connector on the connector of the bolt.

9. The adapter of claim 1, wherein the second end of the body includes a nipple having a circumferential recess, and wherein the lumen of the second connector includes a circumferential recess, the second connector further comprising a washer to engage the circumferential recess of the nipple and the circumferential recess of the lumen to rotatably couple the body to the second connector.

10. A spinal alignment system comprising:
a plurality of pedicle assemblies, each pedicle assembly of the plurality of assemblies including:
   a pedicle screw to engage a pedicle of a vertebra;
   a pedicle post to couple to the pedicle screw and provide mechanical torque to the vertebra;
   an adapter to couple to the pedicle post, the adapter including
      a coupling portion defining a lumen having a central axis to receive the pedicle post;
      an intermediate portion including a first end fixedly attached to a side of the coupling portion, and including a second end distal from the coupling portion, and the intermediate portion is not co-axial with the central axis of the lumen; and
      a bolt, a proximal end of the bolt is pivotally and rotatably coupled to the second end of the intermediate portion and a distal end of the bolt including a threaded coupling;
   a holder to couple to the adapter, the holder having a body and two arms extending from the body, the body having first and second ends and defining a central lumen extending through the body from the first end to the second end, the central lumen to receive the bolt at a first end, the bolt to extend through the second end, the two arms defining upper and lower seats to secure a rod; and
   a nut rotationally coupled to body at the second end, the nut defining a threaded lumen to receive the threaded coupling of the bolt; and
a multipoint alignment system to couple to each holder of each pedicle assembly.

11. The spinal alignment system of claim 10, the multipoint alignment system including: a coronal rod having a handle; a coplanar rod including a slot and a connector configured to attach to the coronal rod; and a first and second transverse rods configured to slideably fit within the slot of the coplanar rod.

12. The spinal alignment system of claim 10, wherein the intermediate portion extending from the coupling portion substantially parallel to the central axis.

13. The spinal alignment system of claim 10, wherein the lumen of the coupling portion has a non-circular cross-section.

14. The spinal alignment system of claim 10, wherein the coupling portion prevents axial and rotational movement of the coupling portion relative to the pedicle post.

15. The spinal alignment system of claim 10, wherein the adapter further includes a release tab to releasably engage the pedicle post.

16. The spinal alignment system of claim 10, wherein the proximal end of the bolt includes a ball joint, and wherein the second end of the intermediate portion defines a socket.

17. The spinal alignment system of claim 10, wherein the two arms of the holder move together in response to a tightening of the nut on the threaded coupling of the bolt.

18. The spinal alignment system of claim 10, wherein the second end of the body of the holder includes a nipple having a circumferential recess, and wherein the lumen of the nut includes a circumferential recess, the nut further comprising a washer to engage the circumferential recess of the nipple and the circumferential recess of the lumen to rotatably couple the body to the nut.

19. An adapter comprising:
   a coupling portion defining a lumen to receive a pedicle post, the lumen having a central axis;
   an intermediate portion extending from the coupling portion substantially parallel to but not co-axial with the central axis, the intermediate portion having a first end fixedly attached to a side of the coupling portion and a second end distal from the coupling portion;
   a bolt, a proximal end of the bolt is pivotally and rotatably coupled to the second end of the intermediate portion and a distal end of the bolt including a connector;
   a holder having a body and two arms extending from the body, the body having first and second ends and defining a central lumen extending through the body from the first end to the second end, the central lumen to receive the bolt at a first end, the bolt to extend through the second end, the two arms defining upper and lower seats to secure a coronal rod; and
   a second connector coupled to body at the second end, the second connector defining a lumen to receive the connector of the bolt.

20. The adapter of claim 19, wherein the connector is a threaded connector.

21. The adapter of claim 19, wherein the lumen of the coupling portion has a noncircular cross-section.

22. The adapter of claim 19, wherein the coupling portion is configured to be coupled to the pedicle post to prevent axial and rotational movement of the coupling portion relative to the pedicle post.

23. The adapter of claim 19, further comprising a release tab configured to releasably engage the pedicle post when a nodule of the release tab is within the lumen of the coupling portion.

24. The adapter of claim 19, wherein the proximal end of the bolt includes a ball joint, and wherein the second end of the intermediate portion defines a socket in which the ball joint is located.

25. The adapter of claim 19, wherein the two arms of the holder pinch in response to connection of the second connector on the connector of the bolt.

26. The adapter of claim 19, wherein the second end of the body includes a nipple having a circumferential recess, and wherein the lumen of the second connector includes a circumferential recess, the second connector further comprising a washer to engage the circumferential recess of the nipple and the circumferential recess of the lumen to rotatably couple the body to the second connector.

* * * * *